US008841106B2

(12) United States Patent
Kobr et al.

(10) Patent No.: US 8,841,106 B2
(45) Date of Patent: *Sep. 23, 2014

(54) PURO-DHFR QUADRIFUNCTIONAL MARKER AND ITS USE IN PROTEIN PRODUCTION

(71) Applicant: Merck Serono SA, Vaud (CH)

(72) Inventors: Michel Kobr, Echandens (CH); Philippe Dupraz, Crissier (CH)

(73) Assignee: Merck Serono SA, Coinsins, Vaud (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/742,495

(22) Filed: Jan. 16, 2013

(65) Prior Publication Data

US 2013/0171714 A1    Jul. 4, 2013

Related U.S. Application Data

(62) Division of application No. 12/601,553, filed as application No. PCT/EP2008/057109 on Jun. 6, 2008, now Pat. No. 8,357,535.

(60) Provisional application No. 60/934,078, filed on Jun. 11, 2007.

(30) Foreign Application Priority Data

Jun. 7, 2007    (EP) .................................... 07109829

(51) Int. Cl.
| | | |
|---|---|---|
| C12N 9/00 | (2006.01) | |
| C12N 15/00 | (2006.01) | |
| G01N 33/74 | (2006.01) | |
| C12N 9/96 | (2006.01) | |

(52) U.S. Cl.
CPC ... *C12N 9/96* (2013.01); *G01N 33/74* (2013.01); *G01N 2333/90666* (2013.01); *C12N 2510/02* (2013.01)
USPC .......................................... 435/183; 435/69.2

(58) Field of Classification Search
None
See application file for complete search history.

(56) References Cited

U.S. PATENT DOCUMENTS

| 2005/0005310 A1 | 1/2005 | Chisholm et al. |
| 2005/0019925 A1 | 1/2005 | Krummen et al. |

FOREIGN PATENT DOCUMENTS

| EP | 1 293 564 | 3/2003 |
| WO | WO 01/04306 | 1/2001 |
| WO | WO 2007/023184 | 3/2007 |

OTHER PUBLICATIONS

Altschul, S. F. et al. "Basic Local Alignment Search Tool" *Journal of Molecular Biology*, 1990, pp. 403-410, vol. 215.
Bennett, R. P. et al. "Fusion of Green Fluorescent Protein with the Zeocin™—Resistance Marker Allows Visual Screening and Drug Selection of Transfected Eukaryotic Cells" *Biotechniques*, 1998, pp. 478-482, vol. 24, No. 3.
Blackwood, E. M. et al. "Going the Distance: A Current View of Enhancer Action" *Science*, 1998, pp. 61-63, vol. 281.
Borth, N. et al. "Efficient Selection of High-Producing Subclones during Gene Amplification of Recombinant Chinese Hamster Ovary Cells by Flow Cytometry and Cell Sorting" *Biotechnol Bioeng*, 2000, pp. 266-273, vol. 71.
Devereux, J. et al. "A comprehensive set of sequence analysis programs for the VAX" *Nucleic Acids Research*, 1984, pp. 387-395, vol. 12, No. 1.
Chesnut, J. D. et al. "Selective isolation of transiently transfected cells from a mammalian cell population with vectors expressing a membrane anchored single-chain antibody" *Journal of Immunological Methods*, 1996, pp. 17-27, vol. 193.
De Felipe, P. et al. "E unum pluribus: multiple proteins from a self-processing polyprotein" *TRENDS in Biotechnology*, Feb. 2006, pp. 68-75, vol. 24, No. 2.
De Wet, J. R. et al. "Cloning of firefly luciferase cDNA and the expression of active luciferase in *Escherichia coli*" *Proc. Natl. Acad. Sci. USA*, Dec. 1985, pp. 7870-7873, vol. 82.
Dufresne, G. et al. "Patent searches for genetic sequences: How to retrieve relevant records from patented sequence database" *Nature Biotechnology*, Dec. 2002, pp. 1269-1271, vol. 20.
Grantham, R. "Amino Acid Difference Formula to Help Explain Protein Evolution" *Science*, Sep. 6, 1974, pp. 862-864, vol. 185, No. 4154.
Kaufman, R. J. et al. "Coamplification and Coexpression of Human Tissue-Type Plasminogen Activator and Murine Dihydrofolate Reductase Sequences in Chinese Hamster Ovary Cells" *Molecular and Cellular Biology*, Jul. 1985, pp. 1750-1759, vol. 5, No. 7.
Kaufman, R. J. et al. "Selection and amplification of heterologous genes encoding adenosine deaminase in mammalian cells" *Proc. Natl. Acad. Sci. USA*, May 1986, pp. 3136-3140, vol. 83.
Kim, N. S. et al. "Key Determinants in the Occurrence of Clonal Variation in Humanized Antibody Expression of CHO Cells during Dihydrofolate Reductase Mediated Gene Amplification" *Biotechnol. Prog.*, 2001, pp. 69-75, vol. 17.
Li, Q. et al. "Locus control regions coming of age at a decade plus" *Trends Genet.*, Oct. 1999, pp. 403-408, vol. 15, No. 10.
Messerle, M. et al. "Structure and Expression of Murine Cytomegalovirus Immediate-Early Gene 2" *Journal of Virology*, Mar. 1991, pp. 1638-1643, vol. 65, No. 3.

(Continued)

*Primary Examiner* — Celine Qian
(74) *Attorney, Agent, or Firm* — Saliwanchik, Lloyd & Eisenschenk

(57) ABSTRACT

This invention relates to industrial production of proteins. More specifically, the invention relates to the res-DHFR surrogate marker, which corresponds to a fusion between DHFR and a protein conferring resistance to a toxic compound or conferring a metabolic advantage. The invention further relates to the use of res-DHFR for screening cells for high expression of a protein of interest. The invention is illustrated by the Puro-DHFR surrogate marker, which corresponds to a fusion between the puromycin N-acetyltransferase and dihydrofolate reductase (DHFR).

4 Claims, 8 Drawing Sheets

(56) References Cited

OTHER PUBLICATIONS

Miller, L. W. et al. "In Vivo protein labeling with trimethoprim conjugates: a flexible chemical tag" *Nature Methods*, Apr. 2005, pp. 255-257, vol. 2, No. 4.

Omasa, T. "Gene Amplification and Its Application in Cell and Tissue Engineering" *Journal of Bioscience and Bioengineering*, 2002, pp. 600-605, vol. 94, No. 6.

Pearson, W.R. et al. "Improved tools for biological sequence comparison" *Proc. Natl. Acad. Sci. USA*, Apr. 1988, pp. 2444-2448, vol. 85.

Pearson, W. R. "Rapid and Sensitive Sequence Comparison with FASTP and FASTA" *Methods in Enzymology*, 1990, pp. 63-98, vol. 183.

Selinger, H. H. et al. "Spectral Emission and Quantum Yield of Firefly Bioluminescence" *Archives of Biochemistry and Biophysics*, 1960, pp. 136-141, vol. 88.

Smith, T. F. et al. "Identification of Common Molecular Subsequences" *J. Mol. Biol.*, 1981, pp. 195-197, vol. 147.

Urlaub, G. et al. "Isolation of Chinese hamster cell mutants deficient in dihydrofolate reductase activity" *Proc. Natl. Acad. Sci. USA*, Jul. 1980, pp. 4216-4220, vol. 77, No. 7.

Wood, K. V. et al. "Synthesis of Active Firefly Luciferase by In Vitro Translation of RNA Obtained from Adult Lanterns" *Biochemical and Biophysical Research Communications*, Oct. 30, 1984, pp. 592-596, vol. 124, No. 2.

Written Opinion in International Application No. PCT/EP2008/057109, Aug. 5, 2008, pp. 1-9.

Miller, L. W. et al. "Methotrexate Conjugates: A Molecular In Vivo Protein Tag" *Angew. Chem. Int. Ed.*, 2004, pp. 1672-1675, vol. 43.

PURO-DHFR QUADRIFUNCTIONAL MARKER AND ITS USE IN PROTEIN PRODUCTION

CROSS-REFERENCE TO RELATED APPLICATIONS

This application is a divisional of U.S. application Ser. No. 12/601,553, filed Nov. 24, 2009, now U.S. Pat. No. 8,357,535, which is the U.S. national stage application of International Patent Application No. PCT/EP2008/057109, filed Jun. 6, 2008, which claims the benefit of U.S. Provisional Patent Application No. 60/934,078, filed Jun. 11, 2007, the disclosures of which are hereby incorporated by reference in their entirety, including all figures, tables and amino acid or nucleic acid sequences.

FIELD OF THE INVENTION

This invention relates to industrial production of proteins. More specifically, the invention relates to the res-DHFR surrogate marker, which corresponds to a fusion between DHFR and a protein conferring resistance to a toxic compound or conferring a metabolic advantage. The invention further relates to the use of res-DHFR for screening cells for high expression of a protein of interest. The invention is illustrated by the Puro-DHFR surrogate marker, which corresponds to a fusion between the puromycin N-acetyltransferase and dihydrofolate reductase (DHFR).

BACKGROUND

Introducing heterologous genes into animal host cells and screening for expression of the added genes is a lengthy and complicated process. Typically a number of hurdles have to be overcome: (i) the construction of large expression vectors; (ii) the transfection and selection of clones with stable long-term expression, eventually in the absence of selective pressure; and (iii) screening for high expression rates of the heterologous protein of interest.

1. Selection of Clones Expressing the Heterologous Gene

Selection of the clones having integrated the gene of interest is performed using a selection marker conferring resistance to a selective pressure. Most of the selection markers confer resistance to an antibiotic such as, e.g., neomycin, kanamycin, hygromycin, gentamycin, chloramphenicol, puromycin, zeocin or bleomycin.

When generating cell clones expressing a gene of interest from expression vectors, host cells are typically transfected with a plasmid DNA vector encoding both the protein of interest and the selection marker on the same vector. Quite often the capacity of a plasmid is limited and the selection marker has to be expressed from a second plasmid, which is co-transfected with the plasmid comprising the gene of interest.

Stable transfection leads to random integration of the expression vector in the genome of the host cell. Use of selective pressure, e.g. by administrating an antibiotic to the media, will eliminate all cells that did not integrate the vector containing the selection marker providing resistance to the respective antibiotic or selective pressure. If this selection marker is on the same vector as the gene of interest or, if this selection marker is on a second vector and vector comprising the gene of interest was co-integrated, the cells will express both the selection marker and the gene of interest. It is frequently observed, however, that the expression level of the gene of interest is highly variable depending on the site of integration.

Furthermore, when removing selective pressure, expression becomes quite often very unstable or even extinguished. Only a small number of initial transfectants are thus providing high and stable long-term expression and it is time-consuming to identify these clones in a large population of candidates. Typically, high expressing candidates are isolated and then cultivated in absence of selective pressure. Under these conditions a large proportion of initially selected candidates are eliminated due to their loss of gene of interest expression upon removal of selective pressure. It would thus be advantageous to cultivate the candidates, following an initial period of selection for stable transfection, in absence of selective pressure and only then screen for gene of interest expression.

2. Screening for High Expressing Clones

Screening for high-expressing clones for a protein of interest is often done by methods directly revealing the presence of high amounts of the protein. Typically immunologic methods, such as ELISA or immunohistochemical staining, are applied to detect the product either intracellularly or in cell culture supernatants. These methods are tedious, expensive, time-consuming, and often not amenable to high throughput screenings (HTS). In addition, an antibody reactive to the expressed protein must be available.

Attempts to quantify the protein amounts by Fluorescence-Activated Cell Sorting (FACS) have also been made, but only with a limited success, especially in the case of secreted proteins (Borth et al., 2000).

One approach for the screening of high expression rates of the protein of interest would be the use of an easily measurable surrogate marker, expressed from the same vector as the gene of interest (Chesnut et al., 1996). The idea underlying the use of a measurable surrogate marker is that there is a correlation between the expression of the gene of interest and the surrogate marker gene due to the physical link of the two genes on the same vector.

Numerous easily measurable markers are available in the art. They usually correspond to enzymes, which act on a chromogenic or luminogenic substrate such as, e.g., the β-glucuronidase, the chloramphenicol acetyltransferase, the nopaline synthase, the β-galactosidase, secreted alkaline phosphatase (SEAP) and the DHFR. The green fluorescent protein (GFP) may also be used as a measurable marker in FACS. The activity of all these proteins can be measured by standard assays that may be used in HTS.

The drawback of this approach is the use of yet another expression cassette for the surrogate marker gene. This renders the expression vector rather bulky, hosting expression units comprising a promoter, a cDNA and polyadenylation signals for at least three proteins (i.e., the gene of interest, the selection marker and the surrogate marker). For multi-chain proteins the situation becomes even more complex. Alternatively, individual plasmid vectors expressing the three genes, which encode the protein of interest, the selection marker and the surrogate marker respectively, could be co-transfected. However, it is likely that the vectors would be either integrated at different loci, or exhibit varying and uncorrelated expression.

A promising approach for overcoming the above limitations consists in the use of a chimeric marker that combines the functional properties of a selection marker and of a measurable marker.

Such bifunctional markers have been described by, e.g., Bennett et al. (1998), Imhof and Chatellard (2006) and Dupraz and Kobr (2007). Bennett et al. (1998) disclose the GFP-Zeo$^R$ marker, which confers resistance to Zeocin antibiotic, which corresponds to a fusion protein between the Green Fluorescent Protein (GFP) and a protein conferring resistance to zeocin. Imhof and Chatellard (2006) disclose the Lupac marker, which corresponds to a fusion between the firefly luciferase protein and a protein conferring resistance to puromycin. Dupraz and Kobr (2007) discloses the PuroLT marker, which corresponds to a fusion protein between the synthetic peptide described by Griffin et al. (1998) and a protein conferring resistance to puromycin.

Miller et al. (2005), in an article showing that fluorescent TMP is an alternative to fluorescent MTX, discloses a fusion protein between a protein conferring resistance to puromycin and a DHFR of bacterial origin. DHFR is used as measurable marker that can be detected by binding to fluorescent MTX or to fluorescent TMP. This article envisions the use of the fusion protein in the field of siRNA gene silencing.

Hence, all markers available for the selection of clones expressing high levels of a recombinant protein correspond to bifunctional markers, which confer resistance to a single toxic compound.

In addition to the bifunctional marker, the vectors used for generating high producer clones usually comprise an amplifiable gene that leads to an increase in copy number when under selective pressure. The copy number of a gene of interest positioned adjacent to the amplifiable gene will also increase, thus leading to the establishment of clones expressing high levels of the protein of interest (Kaufman et al., 1985; Kaufman et al., 1986; Kim et al., 2001; Omasa, 2002). Commonly used amplifiable genes include e.g. dihydrofolate reductase (DHFR), Glutamine synthetase (GS), multiple drug resistance gene (MDR), ornithine decarboxylase (ODC), adenosine deaminase (ADA) and N-(phosphonacetyl)-L-aspartate resistance (CAD).

The finding of a novel and powerful chimeric surrogate marker, conferring resistance to more than one toxic compound and also allowing gene amplification, would be extremely useful in the field of industrial production of therapeutic proteins.

SUMMARY OF THE INVENTION

The present invention stems from the construction and characterization of a novel quadrifunctional marker, Puro-DHFR. Puro-DHFR corresponds to a fusion protein between DHFR and a protein conferring resistance to puromycin, the puromycin N-acetyl transferase (pac). It has been demonstrated that Puro-DHFR combines the functional properties of both pac and DHFR. More specifically, Puro-DHFR is a quadrifunctional marker allowing to (i) select cells for resistance to puromycin; (ii) select cells for resistance to DHFR; (iii) carry out gene amplification; and (iv) sort cells through fluorescence intensity. Puro-DHFR's usefulness for the isolation of high-expressing clones for a therapeutic protein has further been demonstrated.

Therefore, a first aspect of the invention relates to a method of screening cells for expression of a protein of interest, said method comprising the step of:
  a) transfecting cells by an expression vector encoding (i) a res-DHFR chimeric protein comprising a functional fragment of dihydrofolate reductase (DHFR) fused to a fragment conferring resistance to a toxic compound or conferring a metabolic advantage; and (ii) a protein of interest;
  b) selecting cells being resistant to said toxic compound or gaining said metabolic advantage; and
  c) assaying the fluorescence of the cells selected in step (ii) with a fluorescent compound binding to DHFR,
wherein said protein conferring resistance to a toxic compound or conferring a metabolic advantage is not DHFR.

A second aspect of the invention relates to a method of obtaining a cell line expressing a protein of interest, said method comprising the step of:
  a) screening cells according to a method of the invention; and
  b) establishing a cell line from said cells.

A third aspect of the invention relates to a method of producing a protein of interest, said method comprising the step of:
  a) culturing a cell line obtained according to the above method under conditions which permit expression of said protein of interest; and
  b) collecting said protein of interest.

A fourth aspect of the invention relates to a res-DHFR polypeptide comprising a functional fragment of dihydrofolate reductase (DHFR) fused to a fragment conferring resistance to a toxic compound or conferring a metabolic advantage, wherein said protein conferring resistance to a toxic compound or conferring a metabolic advantage is not DHFR.

A fifth aspect of the invention relates to a nucleic acid encoding a res-DHFR polypeptide in accordance with the invention.

A sixth aspect of the invention relates to a res-DHFR vector comprising a nucleic acid in accordance with the invention.

A seventh aspect of the invention relates to a res-DHFR cell comprising a nucleic acid in accordance with the invention.

Further aspects of the invention relate to the use of the res-DHFR cell of the invention for producing a protein of interest, to the use of a res-DHFR polypeptide for screening cells for expression of a protein of interest, to the use of a res-DHFR nucleic acid for screening cells for expression of a protein of interest, and to the use of a res-DHFR vector for screening cells for expression of a protein of interest.

BRIEF DESCRIPTION OF THE FIGURES

FIG. 1A.: pSV40-DHFR-1474; FIG. 1B.: pCMV(IE1)SEAP-IRES-Puro-279; FIG. 1C.: pCMV(IE1)SEAP-IRES-Puro/DHFR-325. 1: gene conferring resistance to ampicillin; 2: f1 origin of replication; 3: synthetic polyadenylation signal; 4: SV40 promoter; 5: mCMV(IE1) promoter; 6: gene conferring resistance to DHFR; 7: SV40 polyadenylation signal; 8: SEAP gene; 9: poliovirus IRES; 10: gene conferring resistance to puromycin (puromycin N-acetyl-transferase); 11: Puro-DHFR marker. All vectors further contain the ColE1-derived plasmid origin of replication.

FIG. 6A: Productivity of alkaline phosphatase (SEAP) FIG. 6B: Gene copy number of the marker (puro-DHFR or puromycin N-acetyl transferase) FIG. 6C: Relative SEAP mRNA expression level.

BRIEF DESCRIPTION OF THE SEQUENCES OF THE INVENTION

Figure 1:
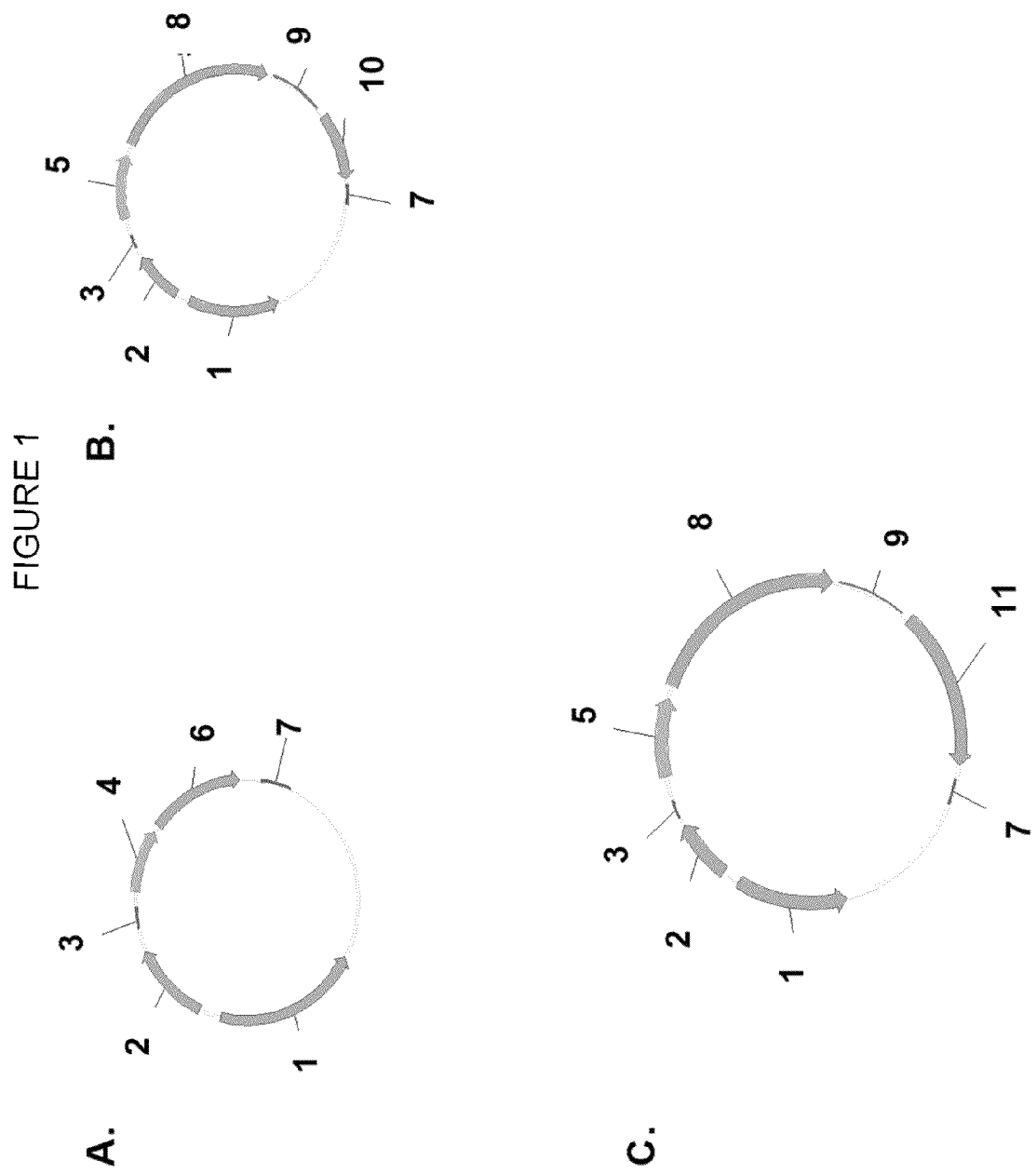
FIG. 1 depicts the plasmids & reporter vectors used in the Examples.

SEQ ID Nos. 1 and 2 respectively correspond to the nucleic acid and to the polypeptide sequences of a Puro-DHFR marker in accordance with the invention.

SEQ ID Nos. 3 and 4 respectively correspond to the nucleic acid and to the polypeptide sequences of *Streptomyces alboniger* puromycin N-acetyl transferase (pac).

SEQ ID Nos. 5 and 6 respectively correspond to the nucleic acid and to the polypeptide sequences of murine DHFR.

SEQ ID Nos. 7 to 10 correspond to primers used when constructing the Puro-DHFR marker in accordance with the invention (Example 1).

SEQ ID Nos. 11 to 16 correspond to oligonucleotides used when detecting the gene copy numbers by QPCR (Example 3).

DETAILED DESCRIPTION OF THE INVENTION

The present invention stems from the construction and characterization of a novel quadrifunctional chimeric marker referred to as res-DHFR. The invention more specifically discloses a res-DHFR polypeptide referred to as Puro-DHFR, which corresponds to a fusion protein between DHFR and a protein conferring resistance to puromycin, the puromycin N-acetyl transferase (pac).

It has been demonstrated that Puro-DHFR is a quadrifunctional marker that combines the functional properties of DHFR and of pac (Example 2). Accordingly, the Puro-DHFR marker can be used:

as a selectable marker in combination with the puromycin toxic compound;
as a selectable marker in combination with the MTX toxic compound;
as an amplifiable gene; and
as an easily measurable surrogate that can be detected both by microscope and by FACS.

Puro-DHFR's usefulness for the isolation of high-expressing clones for a protein of interest has further been demonstrated. In Example 3, a vector comprising Puro-DHFR and a gene of interest, expressed from the same promoter and separated by an IRES, has been constructed. It has been shown that there is a very good positive correlation between Puro-DHFR expression levels and expression levels of the gene of interest.

Accordingly, the present invention provides powerful markers that can be used to provide selectivity in stable transfection, to induce gene amplification of the gene of interest, and which acts as a surrogate marker for screening candidate clones for high expression of a gene of interest. Using res-DHFR, linked to a protein of interest in a bicistronic configuration, allows keeping the same chance for selecting high-expressing clones as when the expression level of the gene of interest is measured directly. Moreover, using res-DHFR allows reducing time, cost and resources since (i) standardized product-independent and simple analysis is performed; and (ii) high expressors can be selected using a FACS.

1. Polypeptides of the Invention

The polypeptide according to the invention is a chimeric protein comprising a functional fragment of a dihydrofolate reductase (DHFR) fused to a fragment conferring either resistance to a toxic compound or a metabolic advantage, wherein said fragment conferring resistance to a toxic compound or a metabolic advantage is not DHFR or a fragment thereof. Such a chimeric protein will further be referred to as "polypeptide in accordance with the invention" or "res-DHFR" within this specification.

The fragment conferring resistance to a toxic compound may be selected from the group consisting of a puromycin N-acetyltransferase (used in combination with the toxic compound puromycin), a neomycin phosphotransferase type II (used in combination with the toxic compound neomycin), a kanamycin phosphotransferase type II (used in combination with the toxic compound kanamycin), a neomycin-kanamycin phosphotransferase type II (used in combination with the toxic compounds neomycin and/or kanamycin), a hygromycin phosphotransferase (used in combination with the toxic compound hygromycin), a gentamycin acetyltransferase (used in combination with the toxic compound gentamycin), a chloramphenicol acetyltransferase (used in combination with the toxic compound chloramphenicol), a zeocin resistance protein (used in combination with the toxic compound zeocin) and a bleomycin resistance protein (used in combination with the toxic compound bleomycin).

In the frame of the present invention "a fragment conferring a metabolic advantage" means that said fragment confers to a cell the ability to grow in the absence of a compound. For example, the glutamine synthetase (GS) protein confers to CHO cells the ability to grow in the absence of glutamine. Thus the fragment conferring a metabolic advantage may e.g. correspond to glutamine synthetase (GS) or a functional fragment thereof.

The term "functional fragment of DHFR" refers to a fragment of a polypeptide that is a member of the dihydrofolate reductase family (EC 1.5.1.3), and that catalyzes the following enzymatic reaction:

5,6,7,8-tetrahydrofolate+NADP$^+$=7,8-dihydrofolate+ NADPH

As used herein, the term "dihydrofolate reductase activity" refers to the catalysis of the above reaction. This activity may be measured, e.g., by determining the ability to confer resistance to the toxic compound methotrexate (MTX) to a cell as described in Example 1.2, or by determining the ability to increase the gene copy number in the presence of MTX as described in Example 1.4. Alternatively, the DHFR activity can be demonstrated by the ability of a DHFR-negative cell transfected with Puro-DHFR to grow in a medium devoid of thymidine and/or hypoxanthine.

In a preferred embodiment, the functional fragment of DHFR is derived from mouse, and is a functional fragment of the sequence of SEQ ID NO: 6. This fragment may comprise at least 50, 75, 100, 125, 150, 175 or 187 amino acids of SEQ ID NO: 6. Most preferably, said functional fragment of DHFR comprises amino acids 200 to 385 of SEQ ID NO: 2.

In a preferred embodiment of the invention, the res-DHFR polypeptide of the invention comprises a fragment of DHFR fused to a fragment of a puromycin N-acetyl transferase (pac), wherein said Puro-DHFR polypeptide exhibits (i) dihydrofolate reductase activity; and (ii) puromycin N-acetyl transferase activity. As further used herein, the term "a Puro-DHFR polypeptide" or "Puro-DHFR" refers to such a polypeptide.

As used herein, a polypeptide exhibits "puromycin N-acetyl transferase activity" when said polypeptide is capable of conferring resistance to puromycin to a cell. The puromycin N-acetyl transferase activity can for example be measured as described in Example 1.2.

The fragment of a puromycin N-acetyl transferase may be derived from a Streptomyces species such as, e.g., *Streptomyces alboniger* or *Streptomyces coelicolor*. Preferably, the Puro-DHFR polypeptide comprises a fragment of a *Streptomyces alboniger* pac. As used herein, the term "*Streptomyces alboniger* pac" refers to a polypeptide of SEQ ID NO: 4 or to an allelic variant, a splice variant or a mutein thereof. More preferably, the pac fragment comprises amino acids 1-199 of SEQ ID NO: 2. Alternatively, said fragment of a *Streptomyces alboniger* pac can comprise at least 50, 75, 100, 125, 150 or 175 amino acids of SEQ ID NO: 4 as long as it retains puromycin N-acetyl transferase activity.

In a Puro-DHFR polypeptide, the DHFR fragment may be fused to the 3' terminus of the pac fragment, or the pac fragment may be fused to the 3' terminus of the DHFR fragment. Preferably, the DHFR fragment is fused to the 3' terminus of the pac fragment.

In a most preferred embodiment, the Puro-DHFR polypeptide comprises or consists of SEQ ID NO: 2.

In another most preferred embodiment, the Puro-DHFR polypeptide comprises or consists of an amino acid sequence at least 50% identical, more preferably at least 60% identical, and still more preferably at least 70%, 75%, 80%, 85%, 90%, 95%, 96%, 97%, 98% or 99% identical to SEQ ID NO: 2.

As used herein, the term "mutein" refers to an analog of a naturally occurring polypeptide, in which one or more of the amino acid residues of a naturally occurring polypeptide are replaced by different amino acid residues, or are deleted, or one or more amino acid residues are added to the naturally occurring sequence of the polypeptide, without lowering considerably the activity of the resulting products as compared with the naturally occurring polypeptide. These muteins are prepared by known synthesis and/or by site-directed mutagenesis techniques, or any other known technique suitable therefore. Muteins of *Streptomyces alboniger* pac or of murine DHFR that can be used in accordance with the present invention, or nucleic acids encoding the muteins, including a finite set of substantially corresponding sequences as substitution peptides or polynucleotides which can be routinely obtained by one of ordinary skill in the art, without undue experimentation, based on the teachings and guidance presented herein.

Muteins of *Streptomyces alboniger* pac or of murine DHFR in accordance with the present invention include proteins encoded by a nucleic acid, such as DNA or RNA, which hybridizes to DNA or RNA, which encodes pac or DHFR, in accordance with the present invention, under moderately or highly stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC.

Muteins of *Streptomyces alboniger* pac or of murine DHFR include polypeptides having an amino acid sequence at least 50% identical, more preferably at least 60% identical, and still more preferably at least 70%, 75%, 80%, 85%, 90%, 95%, 96%, 97%, 98% or 99% identical to the naturally occurring polypeptide.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, or substituted with another amino acid.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux et al., 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul et al., 1990), accessible through the home page of the NCBI at world wide web site ncbi.nlm.nih.gov) and FASTA (Pearson and Lipman, 1988; Pearson, 1990). It is highly preferred that the % identity between two sequences is determined using the KERR algorithm (Dufresne et al., 2002), for example by using a bioinformatic tool such as e.g. GenePAST.

Preferably, the muteins of the present invention exhibit substantially the same biological activity as the naturally occurring polypeptide to which it corresponds.

2. Nucleic Acids, and Vectors and Host Cells Comprising Them

Another aspect of the present invention relates to a nucleic acid that encodes a res-DHFR polypeptide according to the invention.

Preferably, the nucleic acid according to the invention encodes a Puro-DHFR polypeptide. As further used in this specification, the term "Puro-DHFR nucleic acid" refers to such a nucleic acid.

In a preferred embodiment, the Puro-DHFR nucleic acid comprises or consists of SEQ ID NO: 1.

Any procedures known in the art can be used to obtain Puro-DHFR nucleic acids of the present invention. Puro-DHFR nucleic acids can for example be obtained as described in Example 1.

A further aspect of the present invention relates to a vector comprising a nucleic acid in accordance with the invention. A vector comprising a res-DHFR nucleic acid is referred to as a "res-DHFR vector". A vector comprising a Puro-DHFR nucleic acid is referred to as a "Puro-DHFR vector" within the present specification. Preferably, the vector of the invention is an expression vector. The term "vector of the invention" encompasses the term "Puro-DHFR vector".

The term "vector" is used herein to designate either a circular or a linear DNA or RNA compound, which is either double-stranded or single-stranded, and which comprise at least one polynucleotide of the present invention to be transferred in a cell host or in a unicellular or multicellular host organism. An "expression vector" comprises appropriate signals in the vectors, said signals including various regulatory elements, such as enhancers/promoters from viral, bacterial, plant, mammalian, and other eucaryotic sources that drive expression of the inserted polynucleotide in host cells.

In a most preferred embodiment, the vector of the invention further comprises a nucleic acid encoding a protein of interest. As shown in example 3, such vectors are particularly useful for screening cells for high expression of said protein of interest.

In accordance with the present invention, the protein of interest may be any polypeptide for which production is desired. The protein of interest may find use in the field of pharmaceutics, agribusiness or furniture for research laboratories. Preferred proteins of interests find use in the field of pharmaceutics.

For example, the protein of interest may be, e.g., a naturally secreted protein, a normally cytoplasmic protein, a normally transmembrane protein, or a human or a humanized antibody. When the protein of interest is a normally cytoplasmic or a normally transmembrane protein, the protein has preferably been engineered in order to become soluble. The polypeptide of interest may be of any origin. Preferred polypeptides of interest are of human origin.

In preferred embodiments, the protein of interest is selected from the group consisting of chorionic gonadotropin, follicle-stimulating hormone, lutropin-choriogonadotropic hormone, thyroid stimulating hormone, human growth hormone, interferons (e.g., interferon beta-1a, interferon beta-1b), interferon receptors (e.g., interferon gamma receptor), TNF receptors p55 and p75, interleukins (e.g., interleukin-2, interleukin-11), interleukin binding proteins (e.g., interleukin-18 binding protein), anti-CD11a antibodies, erythropoietin, granulocyte colony stimulating factor, granulocyte-macrophage colony-stimulating factor, pituitary peptide hormones, menopausal gonadotropin, insulin-like growth factors (e.g., somatomedin-C), keratinocyte growth factor, glial cell line-derived neurotrophic factor, thrombomodulin, basic fibroblast growth factor, insulin, Factor VIII, somatropin, bone morphogenetic protein-2, platelet-derived growth factor, hirudin, epoietin, recombinant LFA-3/IgG1 fusion protein, glucocerebrosidase, monoclonal antibodies, and muteins, fragments, soluble forms, functional derivatives, fusion proteins thereof.

Preferably, said monoclonal antibody is directed against a protein selected from the group consisting of CD3 (e.g. OKT3, NI-0401), CD11a (e.g. efalizumab), CD4 (e.g. zanolimumab, TNX-355), CD20 (e.g. ibritumomab tiuxetan, rituximab, tositumomab, ocrelizumab, ofatumumab, IMMU-106, TRU-015, AME-133, GA-101), CD 23 (e.g. lumiliximab), CD22 (e.g. epratuzumab), CD25 (e.g. basiliximab, daclizumab), the epidermal growth factor receptor (EGFR) (e.g. panitumumab, cetuximab, zalutumumab, MDX-214), CD30 (e.g MDX-060), the cell surface glycoprotein CD52 (e.g. alemtuzumab), CD80 (e.g. galiximab), the platelet GPIIb/IIIa receptor (e.g. abciximab), TNF alpha (e.g. infliximab, adalimumab, golimumab), the interleukin-6 receptor (e.g. tocilizumab,), carcinoembryonic antigen (CEA) (e.g. 99 mTc-besilesomab), alpha-4/beta-1 integrin (VLA4) (e.g. natalizumab), alpha-5/beta-1 integrin (VLA5) (e.g. volociximab), VEGF (e.g. bevacizumab, ranibizumab), immunoglobulin E (IgE) (e.g. omalizumab), HER-2/neu (e.g. trastuzumab), the prostate specific membrane antigen (PSMA) (e.g. 111In-capromab pendetide, MDX-070), CD33 (e.g. gemtuzumab ozogamicin), GM-CSF (e.g. KB002, MT203), GM-CSF receptor (e.g. CAM-3001), EpCAM (e.g. adecatumumab), IFN-gamma (e.g. NI-0501), IFN-alpha (e.g. MEDI-545/MDX-1103), RANKL (e.g. denosumab), hepatocyte growth factor (e.g. AMG 102), IL-15 (e.g. AMG 714), TRAIL (e.g. AMG 655), insulin-like growth factor receptor (e.g. AMG 479, R1507), IL-4 and IL13 (e.g. AMG 317), BAFF/BLyS receptor 3 (BR3) (e.g. CB1), CTLA-4 (e.g. ipilimumab).

In a preferred embodiment, the vector of the invention is a nucleic acid encoding a protein of interest and comprising at least two promoters, one driving the expression of the polypeptide of the invention, and the other one driving the expression of the protein of interest. Such a vector may further comprise enhancer regions, and/or expression promoting sequences such as insulators, boundary elements, LCRs (e.g. described by Blackwood and Kadonaga (1998) or matrix/scaffold attachment regions (e.g. described by Li et al. (1999).

Alternatively, the vector of the invention comprises a promoter that drives both the expression of the gene of interest and the expression of the polypeptide of the invention. In this embodiment the ORF of the polypeptide of the invention is separated from the ORF of the protein of interest by the presence of sequences such as e.g. an internal ribosomal entry sites (IRES) or a 2A sequence (de Felipe et al., 2006). When a 2A sequence is used, it is preferred that the Puro-DHFR corresponds to the first ORF (i.e. after the promoter) and that the protein of interest corresponds to the second ORF (i.e. after the 2A sequence). The IRES may be derived from, e.g., a virus or a cellular gene. This embodiment is exemplified by the pCMV(IE1)SEAP-IRES-Puro/DHFR-325 vector shown on FIG. 1C, wherein the expression of SEAP gene (8) and of the Puro-DHFR marker (11) is driven by the mCMV(IE1) promoter (5), and wherein the ORFs are separated by an IRES (9).

The term "promoter" as used herein refers to a region of DNA that functions to control the transcription of one or more DNA sequences, and that is structurally identified by the presence of a binding site for DNA-dependent RNA-polymerase and of other DNA sequences, which interact to regulate promoter function. A functional expression promoting fragment of a promoter is a shortened or truncated promoter sequence retaining the activity as a promoter. Promoter activity may be measured in any of the assays known in the art, e.g. in a reporter assay using DHFR as reporter gene (Wood et al., 1984; SELIGER and McELROY, 1960; de Wet et al., 1985), or commercially available from Promega®. An "enhancer region" refers to a region of DNA that functions to increase the transcription of one or more genes. More specifically, the term "enhancer", as used herein, is a DNA regulatory element that enhances, augments, improves, or ameliorates expression of a gene irrespective of its location and orientation vis-à-vis the gene to be expressed, and may be enhancing, augmenting, improving, or ameliorating expression of more than one promoter.

In a preferred embodiment, the vector of the invention comprises at least one promoter of the murine CMV immediate early region. The promoter may for example be the promoter of the mCMV IE1 gene (the "IE1 promoter"), which is known from, e.g., WO 87/03905. The promoter may also be the promoter of the mCMV IE2 gene (the "IE2 promoter"), the mCMV IE2 gene itself being known from, e.g., Messerle et al. (1991). The IE2 promoter and the IE2 enhancer regions are described in details in PCT/EP2004/050280. Preferably, the vector of the invention comprises at least two promoters of the murine CMV immediate early region. More preferably, the two promoters are the IE1 and the IE2 promoters.

In a preferred embodiment, the vector of the invention comprises at least two promoters of the murine CMV immediate early region, wherein one of them drives the expression of a polypeptide of the invention, and the other one drives the expression of a protein of interest.

In another preferred embodiment, the promoters of the murine CMV immediate early region drive the expression of genes encoding a protein of interest, and the Puro-DHFR polypeptide is expressed from an additional expression cassette inserted in the vector backbone. The IE1 and IE2 promoters may drive the expression either of two identical copies of the gene encoding the protein of interest, or of two subunits of a multimeric protein of interest such as antibodies or peptide hormones.

Another aspect of the invention relates to a cell transfected with a res-DHFR nucleic acid of the invention and/or with a res-DHFR vector of the invention. Preferably, said cell is a Puro-DHFR cell transfected with a Puro-DHFR nucleic acid and/or a Puro-DHFR vector. Many cells are suitable in accordance with the present invention, such as primary or established cell lines from a wide variety of eukaryotes including plant and animal cells. Preferably, said cell is a eukaryotic cell. More preferably, said cell is a mammalian cell. Most preferably, said cell is a CHO cell, a human cell, a mouse cell or a hybridoma.

For example, suitable cells include NIH-3T3 cells, COS cells, MRC-5 cells, BHK cells, VERO cells, CHO cells, rCHO-tPA cells, rCHO-Hep B Surface Antigen cells, HEK 293 cells, rHEK 293 cells, rC127-Hep B Surface Antigen cells, CV1 cells, mouse L cells, HT1080 cells, LM cells, Y1 cells, NS0 and SP2/0 mouse hybridoma cells and the like, RPMI-8226 cells, Vero cells, WI-38 cells, MRC-5 cells, Normal Human fibroblast cells, Human stroma cells, Human hepatocyte cells, human osteosarcoma cells, Namalwa cells, human neuronal cells, human retinoblast cells, PER.C6 cells and other immortalized and/or transformed mammalian cells.

3. Methods of Using the Above Polypeptides and Nucleic Acids

Another aspect relates to the use of a cell comprising a res-DHFR nucleic acid according to the invention for producing a protein of interest. Preferably, said cell comprises a Puro-DHFR vector.

As discussed in Example 3, using a Puro-DHFR polypeptide as a selection and surrogate marker provides numerous advantages for screening cells for high expression of a protein of interest. Specifically, since the expression of the Puro-DHFR polypeptide is highly correlated with the expression of the protein of interest, it is advantageous to perform a primary screen for high Puro-DHFR expression, e.g. by FACS. The expression of the protein of interest is assayed in a secondary screen, which is only performed with the best producers isolated further to the primary screen for high Puro-DHFR expression.

Accordingly, another aspect of the invention relates to the use of a polypeptide according to the invention, of a nucleic acid according to the invention or of a vector according to the invention for screening cells for expression or for high expression of a protein of interest. The cells are first screened for high expression of the polypeptide according to the invention (e.g. Puro-DHFR), and expression of the polypeptide according to the invention is then correlated to that of a protein of interest by inference. This allows to rapidly eliminate 80 to 95% of the tested cells based on low expression levels of the polypeptide according to the invention, and to retain the remaining 5-20% for analysis of expression of the gene of interest in a second step.

In the context of the uses and methods of the present invention, the term "high expression" refers to an expression level in a cell that is screened that is higher than in other cells that are screened. "High expression" of a protein is a relative value. For example, final expression levels of recombinant proteins that are commercially produced depend on the protein, annual quantities required and therapeutic dose. During a screening, the expression level of a protein of interest is lower than the final expression level.

A further aspect relates to a method of screening cells for expression or high expression of a protein of interest, said method comprising the step of:

a) transfecting cells by an expression vector encoding res-DHFR;
b) selecting cells being resistant to said toxic compound; and
c) assaying the fluorescence of the cells selected in step (b) with a fluorescent compound binding to DHFR.

Preferably, this method of screening cells for expression or high expression of a protein of interest further comprising the step of amplifying said recombinant protein of interest before performing step (c). Such an amplifying step is preferably performed by growing the cells in the presence of methotrexate (MTX). The concentration of methotrexate will vary depending on the cell type. Typically, CHO cells will be grown in a medium comprising about 50, 75, 100, 125, 150, 200, 300, 500, 1000, 2000, 3000, 4000, 5000 or 6000 nM of MTX for gene amplification.

The fluorescence of the cells may be detected using any fluorescently-labelled folate analogue that covalently binds to DHFR. Such fluorescent compounds include, e.g., fluorescent methotrexate (f-MTX) or fluorescent trimethoprim (f-TMP).

In step (c), the fluorescence may be measured using any apparatus well-known in the art such as, e.g., a fluorescence microscope or a fluorescence-activated cell sorter (FACS) or the like. Using a FACS is particularly advantageous when performing high-throughput screenings.

In a preferred embodiment, the 20% of cells that exhibit highest fluorescence in step (c) comprise the cell that exhibits highest expression of said protein of interest. Preferably, the 10% of cells that exhibit highest fluorescence in step (c) comprise the cell that exhibits highest expression of said protein of interest. Most preferably, the 1% or the 5% of cells that exhibit highest fluorescence in step (c) comprise the cell that exhibits highest expression of said protein of interest.

Any number of cells may be screened by such a method. Preferably, the fluorescence of at least 1, 20, 50, 100, 500, 1,000, 5,000, 10,000, 50,000, 100,000, 500,000, 1,000,000 or 10,000,000 cells is assayed in step (c). Most preferably, a population of cells sufficient for obtaining at least 1,000 to 10,000,000 independent transfectants being resistant to puromycin is screened. Out of these, at least 10 to 1,000,000 candidate clones being resistant to puromycin can further be assayed for fluorescence.

The cells obtained at the end of the above screening method may be ranked relative to each other regarding res-DHFR expression. The cells exhibiting the highest fluorescence may be selected at the end of any of the above methods of screening. For example, individual cells exhibiting DHFR activity corresponding to the top 5-20% of res-DHFR expressors are selected for further analysis of expression of the gene of interest in a subsequent step.

In a preferred embodiment, the above screening method further comprises the step of (d) selecting about 1% to about 20% of the cells assayed in step (c), wherein the selected cells are those exhibiting highest fluorescence in step (c). About 5% to about 20% of the cells assayed in step (c) may be selected based on highest res-DHFR activity. Alternatively, about 1%, 1.5%, 2%, 3%, 4%, 5% to about 30%, 40%, 50%, 60%, 70% or 80% of the cells assayed in step (c) may be selected based on highest res-DHFR activity.

Steps (b) (i.e. selecting resistant cells), (c) (i.e. assaying the fluorescence) and (d) (i.e. selecting the most fluorescent cells) may be iteratively repeated on the population selected at the end of step (d). For example, at least 2, 3, 5 or 10 iterations may be carried out. This may be done with or without changing conditions in between the selection steps. Changing conditions may include e.g. increasing MTX concentration to induce gene amplification or varying culture conditions such as media components or physico-chemical parameters.

Upon selection of the cells exhibiting the highest fluorescence, the expression level of the protein of interest in said selected cells may further be assayed.

Then, the about 1% to about 20% of the cells exhibiting the highest expression of said protein of interest may be selected. For example, about 1%, 1,5%, 2%, 3%, 4%, 5% to about 15%, 18% or 20% of the cells exhibiting the highest expression of said protein of interest may be selected. Preferably, the cell exhibiting the highest expression of said protein of interest is selected. This selection based on expression of the protein of interest is preferably performed after the last iteration of step (d) (i.e. the last selection based on fluorescence).

A further aspect of the invention pertains to a method of obtaining a cell line expressing a protein of interest, said method comprising the steps of:
 a) screening cells according to the above method; and
 b) establishing a cell line from said cells.

As used herein, a "cell line" refers to one specific type of cell that can grow in a laboratory. A cell line can usually be grown in a permanently established cell culture, and will proliferate indefinitely given appropriate fresh medium and space. Methods of establishing cell lines from isolated cells are well-known by those of skill in the art.

Another aspect relates to a method of producing a protein of interest, said method comprising the step of:
 a) culturing a cell line obtained as described above under conditions which permit expression of said protein of interest; and
 b) collecting said protein of interest.

Conditions which permit expression of the protein of interest can easily be established by one of skill in the art by standard methods. For example, the conditions disclosed in Example 3.3.1 may be used.

In a preferred embodiment, the above method of producing a protein of interest further comprises the step of purifying said protein of interest. The purification may be made by any technique well-known by those of skill in the art. In the case of a protein of interest for use in the field of pharmaceutics, the protein of interest is preferably formulated into a pharmaceutical composition.

The invention further pertains to the use of a res-DHFR polypeptide for screening cells for expression of a protein of interest, to the use of a res-DHFR nucleic acid for screening cells for expression of a protein of interest, and to the use of a res-DHFR vector for screening cells for expression of a protein of interest. The res-DHFR polypeptide, nucleic acid or vector preferably is a Puro-DHFR polypeptide, nucleic acid or vector.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Example 1

Protocols 1.1. Construction of the Puro-DHFR Nucleic Acid

The constructs described hereinbelow are depicted in FIG. 1. All constructs are based on the pGL3-basic plasmid backbone (Promega).

The fusion protein between the puromycin resistance gene and wild type murine DHFR was obtained by recombinant PCR. Part of the poliovirus IRES and the complete puromycin resistance gene ORF (omitting the stop codon) that are present in vector pmCMV(IE1)-SEAP-IRES-PuroR-p279 were amplified by PCR using primers of SEQ ID Nos. 7 and 8 and a high fidelity DNA polymerase (HS-KOD; Novagen). The wild-type murine DHFR ORF and part of the SV40 late polyadenylation signal present in plasmid pSV40-DHFR (p1474) were amplified using primers of SEQ ID Nos. 9 and 10.

To generate the fusion Puro-DHFR marker, the resulting PCR products were mixed and reamplified using primers of SEQ ID Nos. 7 and 10 and cloned into a vector wherein the murine IE1 promoter drives the expression of the human placental alkaline phosphatase gene (SEAP) and the Puro-DHFR selection marker is expressed as the second cistron placed downstream of the poliovirus IRES. The integrity of all elements amplified by PCR was verified by sequencing. This vector is further referred to as pmCMV(IE1)-SEAP-IRES-Puro/DHFR-p325 or p325.

1.2. Transfection and Cell Culture

Figure 2:
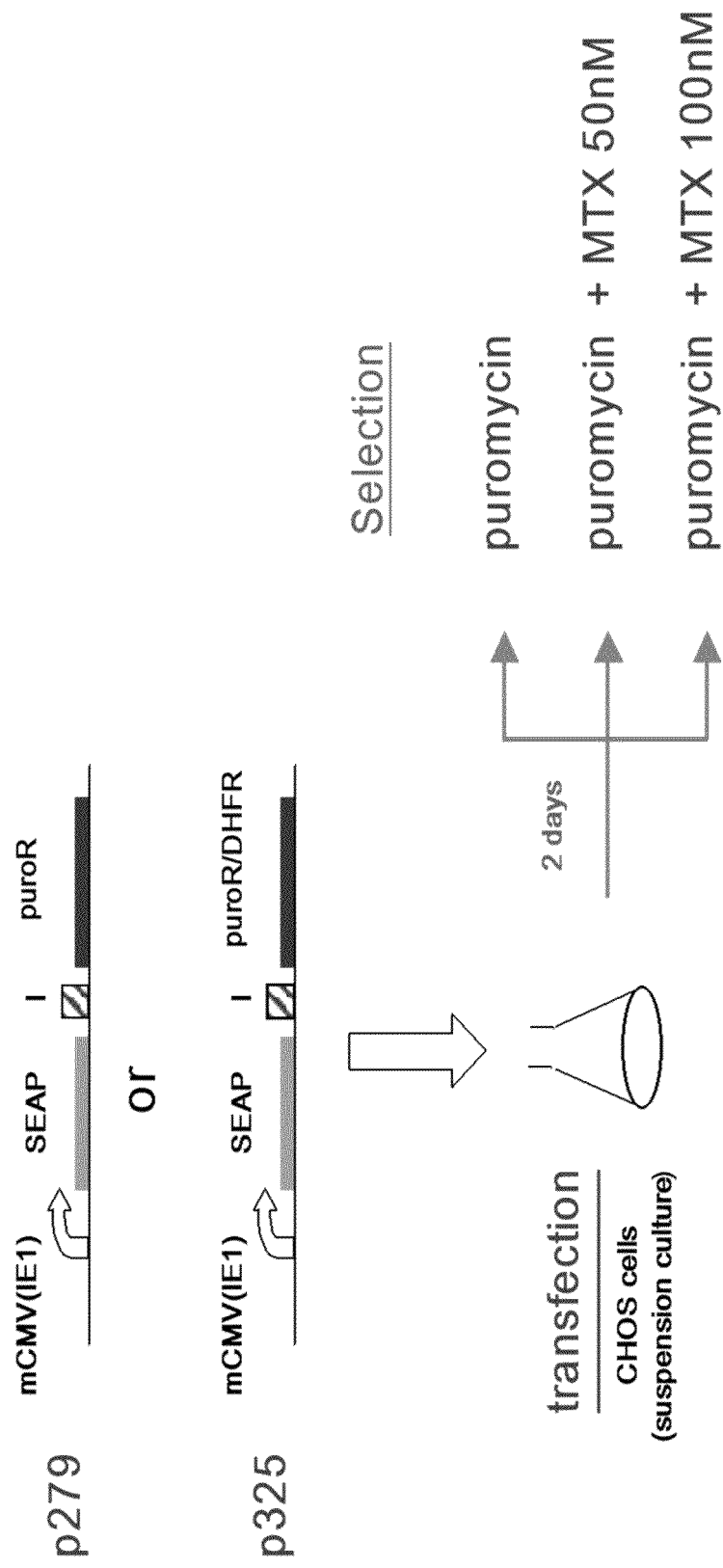
FIG. 2 is a scheme representing the experiment for selecting clones transfected with the plasmids & reporter vectors.

The protocol for selecting stable transfectants is schematized in FIG. 2.

CHO-S cells were derived from the Chinese hamster ovaries and adapted to serum-free suspension culture (Invitrogen/Gibco, La Jolla, Calif.). CHO DX11-F10 is a cell line derived from the DHFR-deficient CHO DUKXB11 cell line (Urlaub et al. 1980) that was adapted to growth in suspension in serum-free media. Both cells are routinely cultivated in ProCho5 (Lonza Biologics). The medium for cultivation of DXB11-F10 cells was supplemented with hypoxanthine (100 µM) and thymidine (16 µM) (HT supplement; Invitrogen/Gibco) unless the contrary is indicated.

CHO-S and DXB11-F10 cells were transfected using polyethylenimine (linear PEI 25 kd). Cells were plated in 6-well plates in 2.5 mL RPMI-1640 (Invitrogen/Gibco) plus 0.05% Pluronic F68 (Sigma) at a concentration of $5 \times 10^5$ cells per mL. 5 µg of linearized plasmid DNA in 250 µl of 150 mM NaCl was mixed with a solution of 15 µl of 1 mM linear PEI25 diluted in 250 µl of 150 mM NaCl. The PEI:DNA complexes were allowed to form for 5 minutes at room temperature and are then added to the cells. After 3 hours the transfection medium is replaced with serum-free culture medium.

48 hours post-transfection selection was applied and the medium changed 2 times per week until cells recovered and cell viability was greater than 90%.

For selection, puromycin was used at 10 µg/ml and the folate analogue methotrexate (Calbiochem) was used at a concentration of 50 to 100 nM.

For amplification studies, clones were first obtained by limited dilution at 0.3 cell per well in 384-well plates under selection with puromycin at 10 µg/ml. Clones were then cultivated for 4 weeks under selection with puromycin (10 µg/ml) or puromycin plus methotrexate (100 nM). Genomic DNA was then extracted and reporter gene copy number was determined by QPCR.

1.3. Determination of Reporter Gene Expression by SEAP Assay

Stably transfected cell pools were seeded at $2.5 \times 10^5$ cells/ml in 125 ml shake-flasks and grown for up to 7 days in batch culture. Cell culture media was harvested at various time points and to avoid day-to-day variation in the SEAP measurements the samples were kept at −20° C. until analysis. Relative SEAP activity was determined in a kinetic enzyme assay. 10 µl of serial dilutions of media in hepes-buffered saline solution (HBSS) were added to a 96-well plate then 100 µl of a Phosphatase Substrate Solution (Pierce) was added to each well and readings of OD at 405 nM were taken at regular time intervals. Only the linear window of the plot OD vs. time was considered for analysis.

1.4. Determination of Gene Copy Number by QPCR.

Genomic DNA was isolated using the GenElute Mammalian Genomic DNA Miniprep kit (Sigma) according to the manufacturer's instructions and quantified spectrophotometrically. For determination of gene copy number 10ng of genomic DNA were analyzed by quantitative PCR with the 7500 Real-Time PCR instrument (Applied Biosystems) using standard cycling conditions in a multiplex assay. A puromycin-specific TaqMan probe was used to detect the reporter construct and second TaqMan probe, detecting the hamster glyceraldehyde phosphate dehydrogenase (GAPDH) gene was used as an endogenous control. A standard curve was generated using genomic DNA from cell lines in which the puromycin gene copy number had been determined by Southern blot.

The oligonucleotides had the sequences of SEQ ID Nos. 11, 12 and of FAM-SEQ ID NO: 13-BHQ1 for detection of the puromycin acetyltransferase gene, and of SEQ ID Nos. 14, 15 and of YY-SEQ ID NO: 16-BHQ1 for detection of the GAPDH gene. FAM and YY are abbreviations for fluorophores 5-carboxyfluorescein and Yakima Yellow respectively (Epoch Biosciences). BHQ1™ (Biosearch Technologies, Inc.) is a quencher linked to the 3' of the TaqMan probes.

Core PCR reagents were from Applied Biosystems and 96-well detection plates were obtained from AxonLab.

1.5. Determination of Relative Reporter Gene Expression by Reverse Transcriptase-QPCR.

Total RNA was isolated from $\sim 5 \times 10^6$ cells using the NucleoSpin RNA II kit (Macherey-Nagel)-which includes a DNase treatment step—and RNA concentration was determined spectrophotometrically at 260 nm.

Relative quantification of the reporter expression was performed by One-Step Reverse Transcriptase-QPCR (One-Step RT-PCR Master Mix Reagent; Applied Biosystems) on 25 ng of total RNA using the Puro and GAPDH primers and Taq- Man probes described above. GAPDH served as an endogenous control. The amounts of the reporter mRNA were calculated by the ΔΔCt method and expressed relative to the pool p279 (selected with puromycin only).

1.6. Labeling with Fluorescein-Methotrexate 2.5-5×10$^5$ cells were incubated over-night at 29° C. in 0.5 mL of culture medium containing 10 mM fluorescein-labeled methotrexate (F-MTX, Molecular Probes/Invitrogen). Labeled cells were washed in serum-free culture medium and images were recorded using a fluorescence microscope (Olympus CKX41 microscope equipped with a DP50 digital camera) using a FITC filter set.

Example 2

Puro-DHFR is a Quadrifunctional Marker 2.1. Puro-DHFR Confers Resistance to Puromycin to the Transfected Cells (i.e. Puro-DHFR has Puromycin Acetyltransferase Activity)

Figure 3:
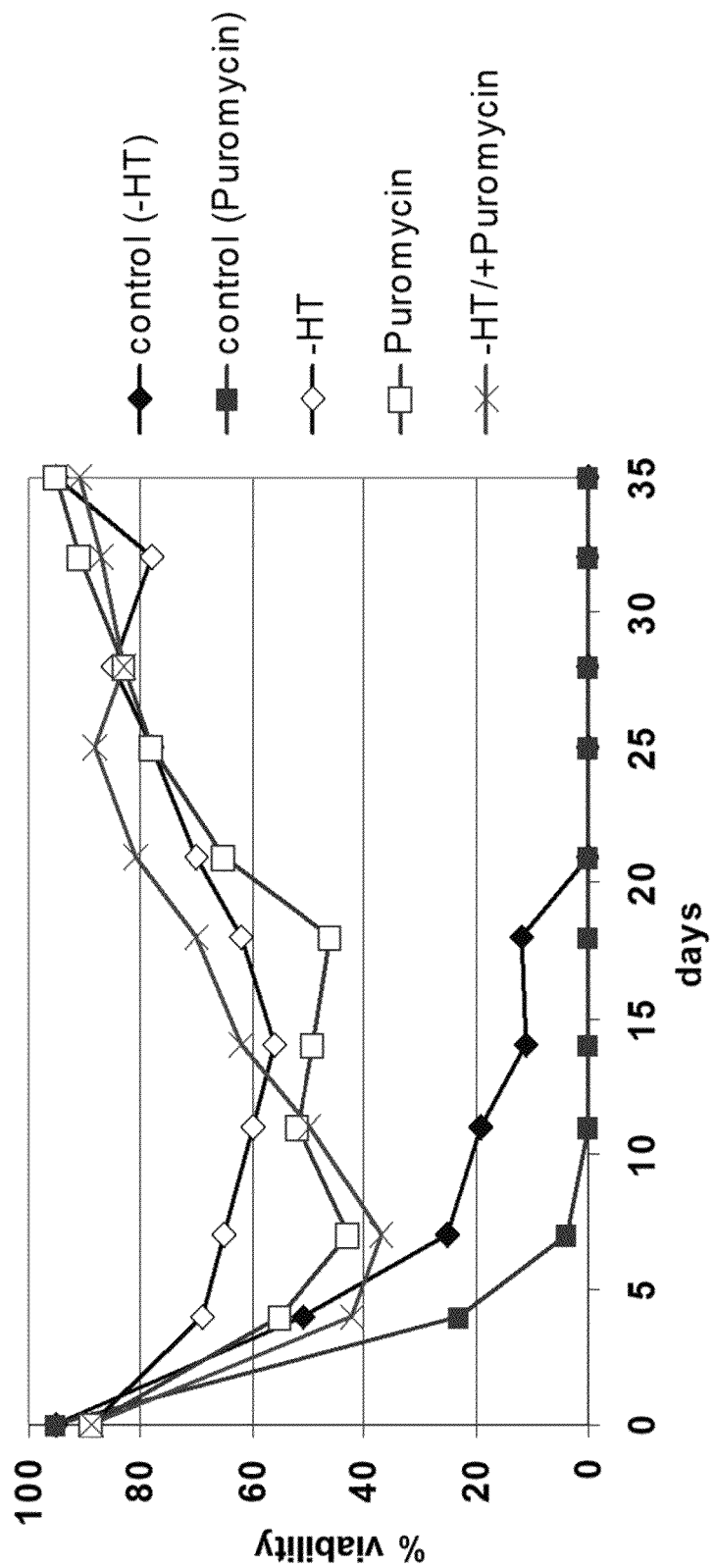
FIG. 3 compares the viability of DXB11-F10 CHO cells transfected with the pCMV(IE1)SEAP-IRES-Puro/DHFR-325 vector with the viability of untransfected DXB11-F10 CHO cells (control) during the selection process. The experiment was performed in the absence of HT and in the absence of puromycin (-HT), in the presence of HT and in the presence of puromycin at 10 mg/L (Puromycin), and in the absence of HT and in the presence of puromycin (-HT/Puromycin).

CHO DXB11-F10 cells were transfected with the p325 vector encoding Puro-DHFR as described in Example 1.2. As shown on FIG. 3, the Puro-DHFR selection marker confers puromycin resistance to the transfected cells.

2.2. Puro-DHFR Allows Growth in Absence of HT (i.e. Puro-DHFR has DHFR Activity)

DHFR-deficient cells are sensitive to MTX and require the presence of HT (Hypoxanthine and Thymidine) in the culture medium for growth.

DHFR-deficient CHO DXB11-F10 cells were transfected with the p325 vector encoding Puro-DHFR as described in Example 1.2. As shown on FIG. 3, the Puro-DHFR selection marker allows growth of p325-transfected DXB11-F10 cells in the absence of HT.

2.3. Puro-DHFR Induces Gene Amplification

CHO-S cells, which endogenously express DHFR, were transfected with the p325 vector encoding Puro-DHFR as described in Example 1.2. The cells were selected in the presence of puromycin (10 μg/ml). Clones were obtained by limited dilution of the resistant population. Interestingly, the experiments shown here demonstrate that Puro-DHFR selection and amplification is feasible in CHO-S cells despite its endogenous DHFR background expression.

Twenty randomly selected clones were cultivated either in the presence of puromycin (10 μg/ml) or in the presence of puromycin and 100 nM MTX for 4 weeks in order to test for gene amplification.

Figure 8:
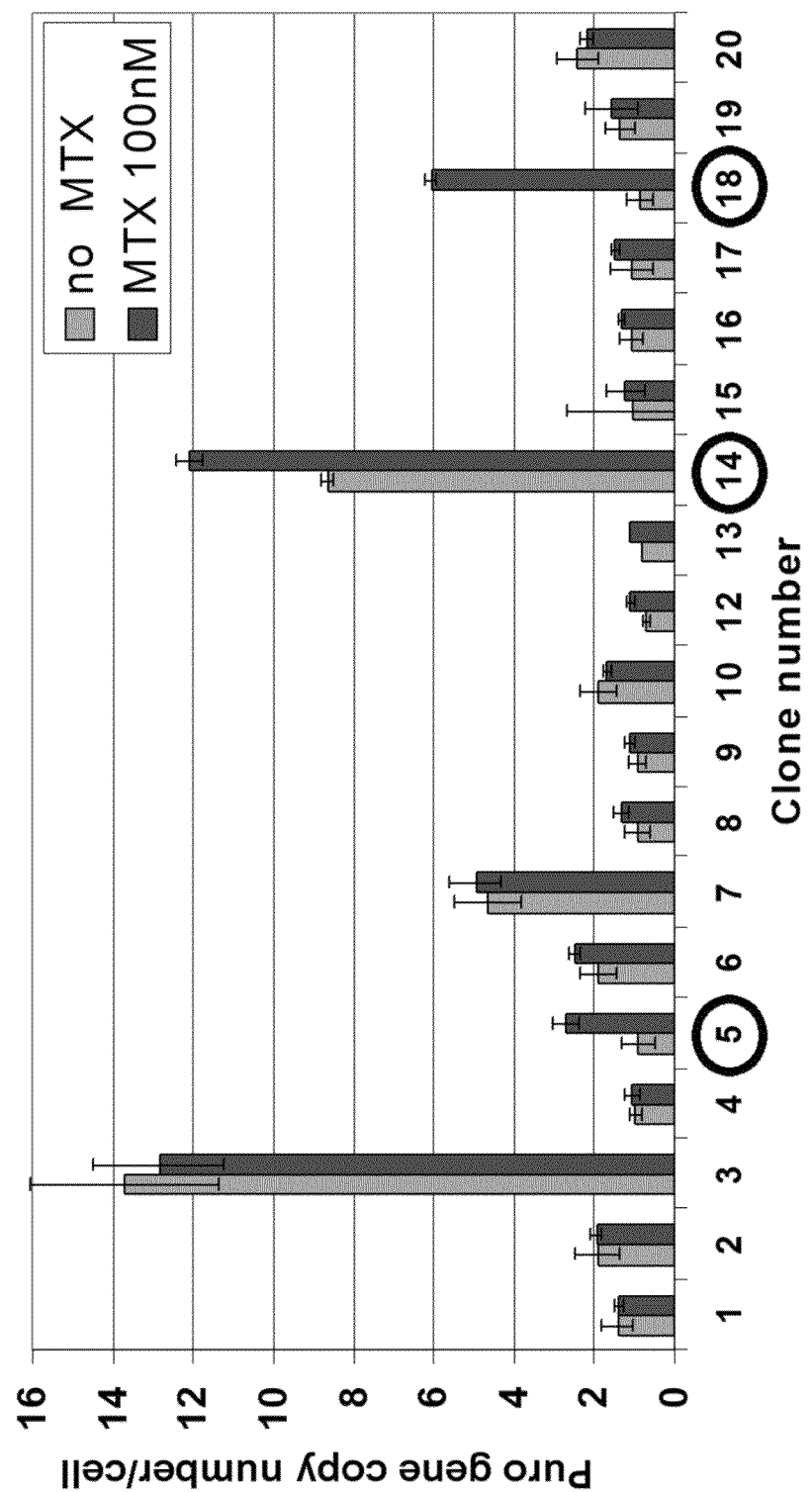
FIG. 8 shows the changes in Puro-DHFR copy number in clones of CHO-S cells stably transfected with pmCMV (IE1)—SEAP-IRES-Puro-DHFR-325 after cultivation in selective medium containing either puromycin or puromycin plus 100 nM MTX.

The gene copy number was then determined for pools of transformed cells as described in Example 1.4. As shown on FIG. 8, amplification of gene copy number depends upon selection with MTX. In 3 of 20 clones re-selected with puromycin plus MTX at 100 nM (circled) reporter copy number is increased compared to selection with puromycin only, demonstrating the potential for gene amplification.

2.4. Puro-DHFR can be Detected Through its Fluorescence

Figure 5:
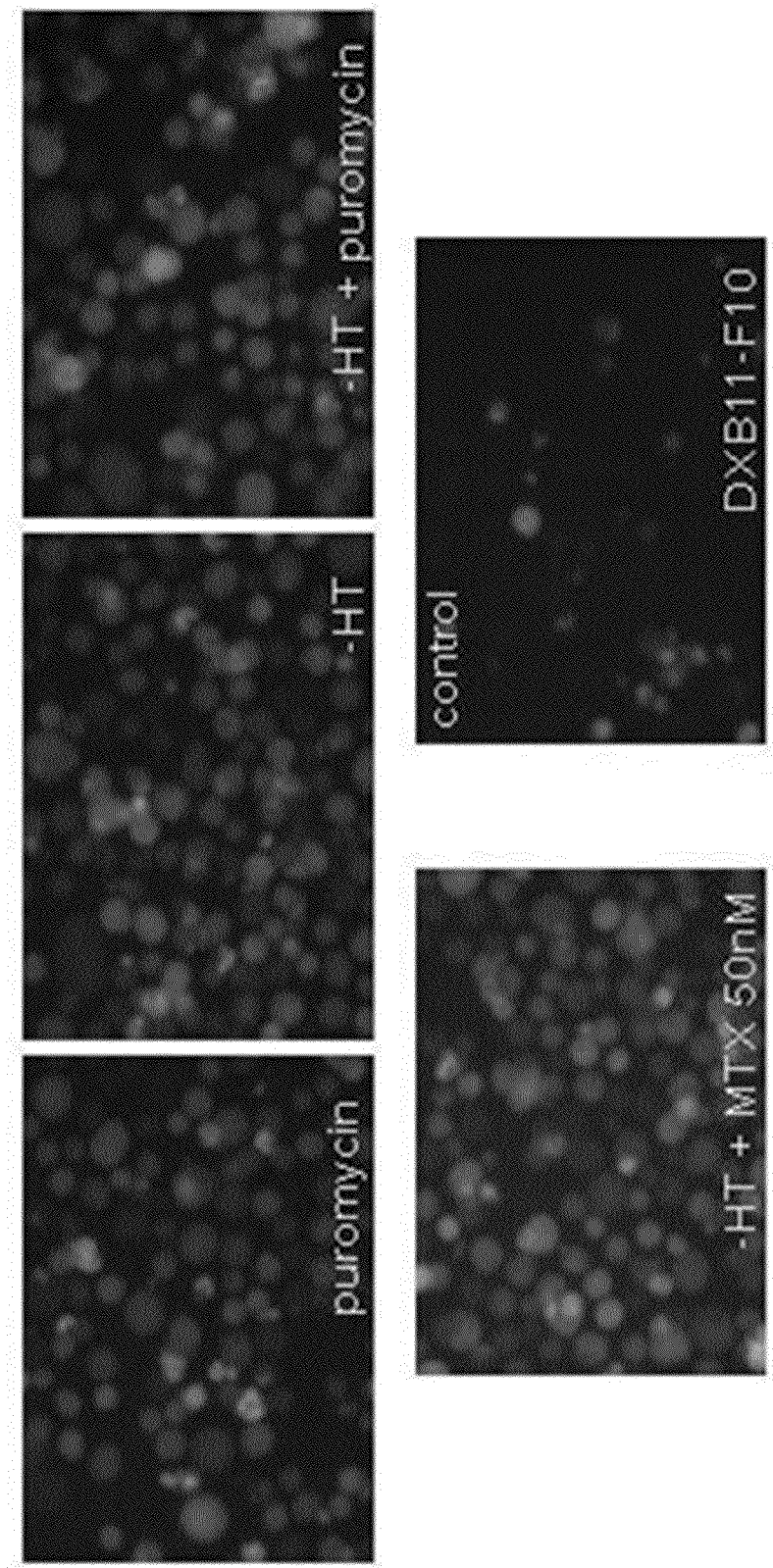
FIG. 5 shows the fluorescence of DXB11-F10 CHO cells transfected with the pCMV(IE1)SEAP-IRES-Puro/DHFR-325 vector grown in different selection media and stained with fluorescent methotrexate (F-MTX).

FIG. 5 shows labeling with fluorescent methotrexate of CHO DXB11-F10 cells transfected with the p325 vector encoding Puro-DHFR. Florescence was detected as described in Example 1.6. The untransfected DXB11-F10 cells are much less fluorescent than the transfected ones. In addition, higher selection pressure in presence of MTX (50 nM) leads to increased expression of the puro-DHFR selection marker and more intense cell labeling.

Figure 7:
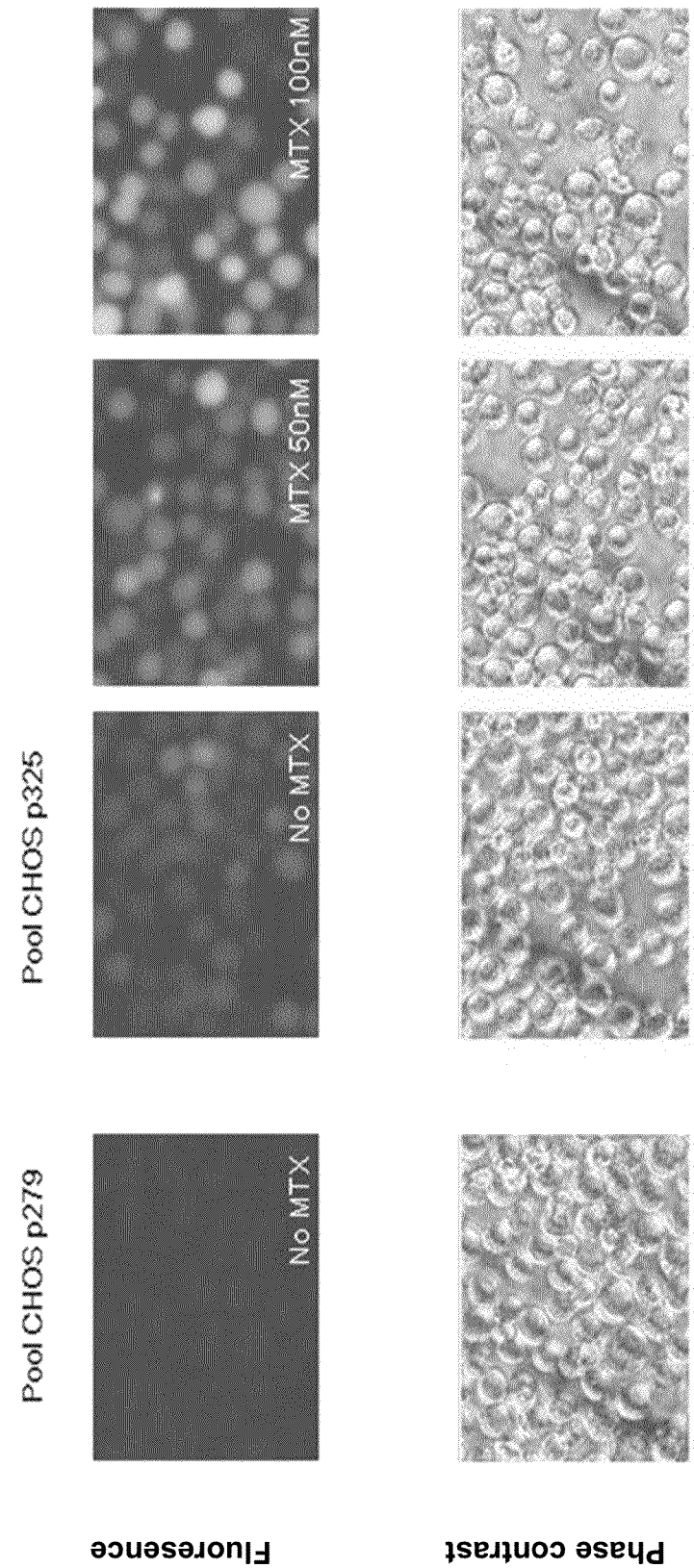
FIG. 7 shows the fluorescence of CHO-S cells transfected either with the pCMV(IE1)SEAP-IRES-Puro/DHFR-325 vector (p325) or with the pCMV(IE1)SEAP-IRES-Puro-279 vector (p279) grown in different selection media. "Phase contrast" corresponds to the optical technique used to generate images of biological samples based on differences of the refractive index of the specimen in white light.

FIG. 7 shows labeling with fluorescent methotrexate of CHO-S cells transfected with the p325 vector encoding Puro-DHFR. The background levels of fluorescence in pools of CHO-S p279 (expressing only the endogenous DHFR gene) is significantly lower than fluorescence in pools of CHO-S p325 cells selected at high levels of MTX.

Thus Puro-DHFR can be detected both in DHFR+ (CHO-S) and in DHFR− (CHO-DXB11-F10) cells.

Example 3

Figure 4:
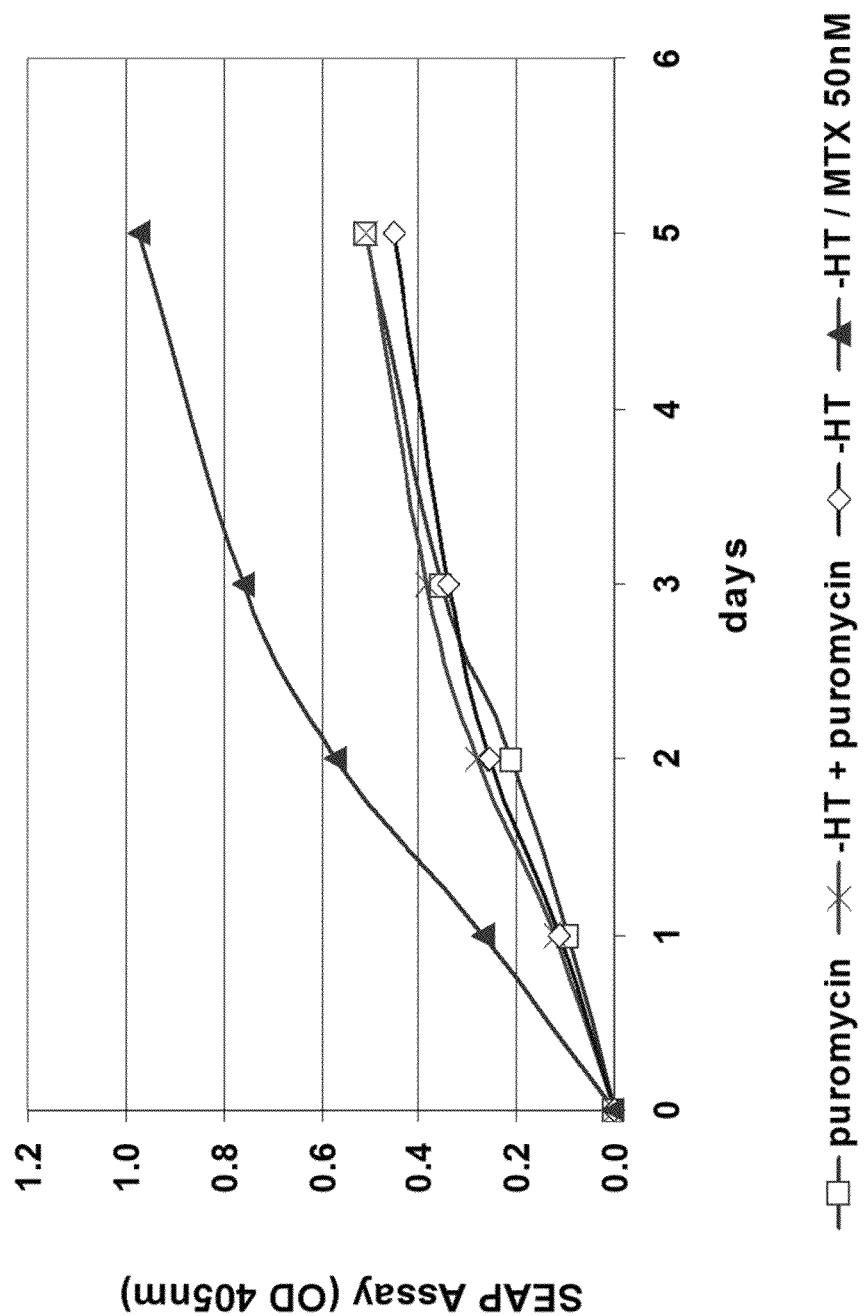
FIG. 4 shows the productivity of alkaline phosphatase (SEAP) in batch cultures of DXB11-F10 CHO cells transfected with the pCMV(IE1)SEAP-IRES-Puro/DHFR-325 vector. The experiment was performed in the absence of HT and in the absence of puromycin (-HT), in the presence of HT and in the presence of puromycin at 10 mg/L (Puromycin), in the absence of HT and in the presence of puromycin (-HT/Puromycin), and in the absence of HT and in the presence of MTX (50 nM) (-HT/MTX).

Puro-DHFR is a Surrogate Marker Useful for Screening for Cells Expressing High Levels of a Protein of Interest 3.1. Puro-DHFR Allows Isolating Clones Expressing High Levels of a Protein of Interest DXB11-F10 cells were transfected with the p325 vector encoding Puro-DHFR. This vector additionally comprises SEAP as a reporter gene (protein of interest). Stable pools were selected in presence or in the absence of MTX, and expression of SEAP was measured as described in Example 1.3. As shown on FIG. 4, pools selected in the presence of MTX exhibited about 2-fold higher SEAP expression than pools selected with puromycin or in absence of HT only.

Figure 6:
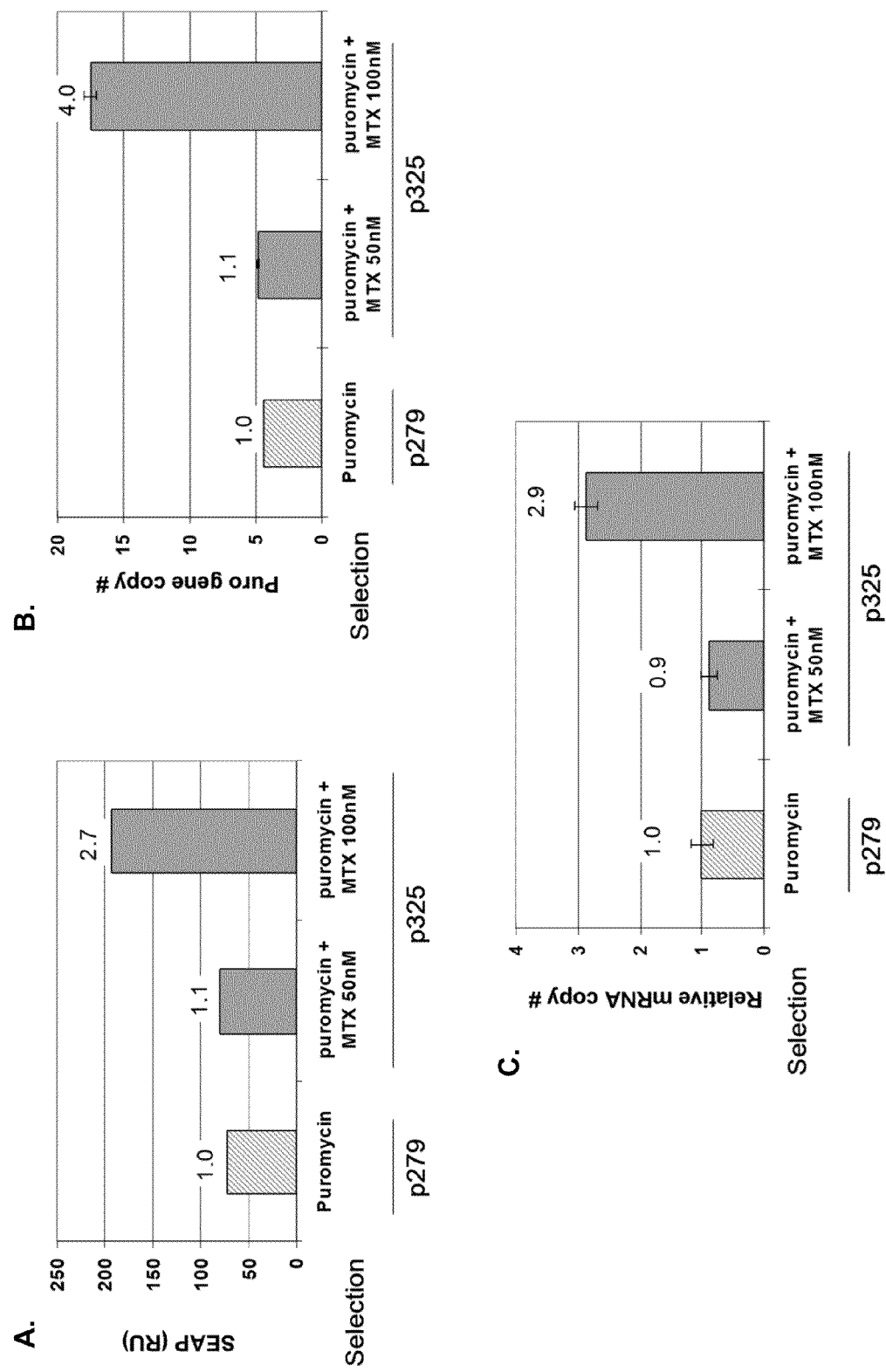
FIGS. 6A-6C compare CHO-S cells transfected with the pCMV(IE1)SEAP-IRES-Puro/DHFR-325 vector that encodes the puro-DHFR marker (p325) with CHO-S cells transfected with the pCMV(IE1)SEAP-IRES-Puro-279 vector that encodes puromycin N-acetyl transferase (p279).

CHO-S cells were transfected either with the p325 vector encoding Puro-DHFR or with the p279 vector encoding puromycin N-acetyltransferase and SEAP. Stable pools were selected in presence of puromycin and of 0, 50 or 100 nM MTX. Expression of SEAP was measured at day 7 both as described in Example 1.3a and in Example 1.5. FIG. 6 shows that increased selection pressure of CHO-S p325 stable pool with puromycin plus MTX (100 nM) leads to significantly higher expression of SEAP protein, both at the protein level (A) and at the mRNA level (B).

Thus the puro-DHFR marker allows isolating clones expressing higher levels of the SEAP protein than prior art markers such as puromycin N-acetyltransferase.

3.2. Puro-DHFR can be Used as a Surrogate Marker in High-Throughput Screenings

Puro-DHFR is used as a selective and surrogate marker to establish and screen candidate clones with a vector expressing both Puro-DHFR and the protein of interest. After transfection, selection and amplification, a primary screen is done by FACS for fluorescence (i.e. high Puro-DHFR expression) with a high probability of selecting clones that also exhibit high gene of interest expression. Then a second screen is performed for expression of the protein of interest, possibly directly by ELISA.

Using Puro-DHFR in high throughput screening (HTS) thus allows keeping the same chance for selecting high expressing clones, and allow reducing time and resources. In addition, it is important to note that the fusion of two individual enzymes with so different activities and origins surprisingly retains their function in Puro-DHFR as it is described here. Indeed, Puro-DHFR can truly be used to provide selectivity in stable transfection, act as an amplifiable gene, and act as a surrogate marker for screening candidate clones for high expression of a gene of interest.

REFERENCES

Altschul, S. F., Gish, W., Miller, W., Myers, E. W., and Lipman, D. J. (1990). Basic local alignment search tool. J. Mol. Biol. 215:403-410.

Bennett, R. P., Cox, C. A., and Hoeffler, J. P. (1998). Fusion of green fluorescent protein with the Zeocin-resistance marker allows visual screening and drug selection of transfected eukaryotic cells. Biotechniques 24:478-482.

Blackwood, E. M. and Kadonaga, J. T. (1998). Going the distance: a current view of enhancer action. Science 281: 61-63.

Borth, N., Zeyda, M., Kunert, R., and Katinger, H. (2000). Efficient selection of high-producing subclones during gene amplification of recombinant Chinese hamster ovary cells by flow cytometry and cell sorting. Biotechnol. Bioeng. 71:266-273.

Chesnut, J. D., Baytan, A. R., Russell, M., Chang, M. P., Bernard, A., Maxwell, I. H., and Hoeffler, J. P. (1996). Selective isolation of transiently transfected cells from a mammalian cell population with vectors expressing a membrane anchored single-chain antibody. J. Immunol. Methods 193:17-27.

de Felipe, P., Luke, G. A., Hughes, L. E., Gani, D., Halpin, C., and Ryan, M. D. (2006). E unum pluribus: multiple proteins from a self-processing polyprotein. Trends Biotechnol. 24, 68-75.

de Wet, J. R., Wood, K. V., Helinski, D. R., and DeLuca, M. (1985). Cloning of firefly DHFR cDNA and the expression of active DHFR in *Escherichia coli*. Proc Natl Acad Sci USA 82:7870-7873.

Devereux, J., Haeberli, P., and Smithies, O. (1984). A comprehensive set of sequence analysis programs for the VAX. Nucleic Acids Res. 12:387-395.

Dufresne, G., Takacs, L., Heus, H. C., Codani, J. J., and Duval, M. (2002). Patent searches for genetic sequences: how to retrieve relevant records from patented sequence databases. Nat. Biotechnol. 20, 1269-1271.

Dupraz, P. and Kobr, M. (2007). System for screening cells for high expression of a protein of interest. WO 2007/023184.

Grantham, R. (1974). Amino acid difference formula to help explain protein evolution. Science 185:862-864.

Imhof, M., and Chatellard, P. (2006). The LUPAC bifunctional marker and its use in protein production. WO 2006/058900.

Kaufman, R. J., Wasley, L. C., Spiliotes, A. J., Gossels, S. D., Latt, S. A., Larsen, G. R., and Kay, R. M. (1985). Coamplification and coexpression of human tissue-type plasminogen activator and murine dihydrofolate reductase sequences in Chinese hamster ovary cells. Mol. Cell. Biol. 5:1750-1759.

Kaufman, R. J., Murtha, P., Ingolia, D. E., Yeung, C. Y. and Kellems, R. E. (1986). Selection and amplification of heterologous genes encoding adenosine deaminase in mammalian cells. Proc. Natl. Acad. Sci. U.S.A. 83:3136-3140.

Kim, N. S., Byun, T. H. and Lee, G. M. (2001). Key determinants in the occurrence of clonal variation in humanized antibody expression of cho cells during dihydrofolate reductase mediated gene amplification. Biotechnol. Prog. 17:69-75.

Li, Q., Harju, S., and Peterson, K. R. (1999). Locus control regions: coming of age at a decade plus. Trends Genet. 15:403-408.

Messerle, M., Keil, G. M., and Koszinowski, U. H. (1991). Structure and expression of murine cytomegalovirus immediate-early gene 2. J. Virol. 65, 1638-1643.

Miller, L. W., Cai, Y., Sheetz, M. P., Cornish, V. W. (2005). In vivo protein labeling with trimethoprim conjugates: a flexible chemical tag. Nat. Methods. 2:255-257.

Omasa, T. (2002). Gene amplification and its application in cell and tissue engineering. J. Biosci. Bioeng. 94:600-605.

Pearson, W. R. and Lipman, D. J. (1988). Improved tools for biological sequence comparison. Proc. Natl. Acad. Sci. U.S.A., 85, 2444-2448.

Pearson, W. R. (1990). Rapid and sensitive sequence comparison with FASTP and FASTA. Methods Enzymol. 183, 63-98.

Seliger, H. H. and McElroy, W. D. (1960). Spectral emission and quantum yield of firefly bioluminescence. Arch. Biochem. Biophys. 88, 136-141.

Smith, T. F. and Waterman, M. S. (1981). Identification of common molecular subsequences. J. Mol. Biol. 147, 195-197.

Urlaub, G. and Chasin, L. A. (1980). Isolation of Chinese hamster cell mutants deficient in dihydrofolate reductase activity. Proc. Natl. Acad. Sci. U.S.A. 77:4216-4220.

Wood, K. V., de Wet, J. R., Dewji, N., and DeLuca, M. (1984). Synthesis of active firefly DHFR by in vitro translation of RNA obtained from adult lanterns. Biochem Biophys. Res. Commun. 124, 592-596.

We claim:

1. An isolated Puro-DHFR polypeptide comprising SEQ ID NO: 2, said polypeptide having: (i) puromycin N-acetyl transferase activity; and (ii) dihydrofolate reductase activity.

2. A method of producing a protein of interest comprising expressing a first nucleic acid encoding a polypeptide of interest and a second nucleic acid encoding a polypeptide according to claim 1 in a host cell under conditions permitting the expression of said polypeptide of interest.

3. The method according to claim 2, said method further comprising the purification of said protein of interest.

4. A method of expressing a polypeptide having puromycin N-acetyl transferase activity and dihydrofolate reductase activity comprising expressing a nucleic acid encoding a polypeptide according to claim 1 in a host cell under conditions permitting the expression of said polypeptide.

* * * * *

SEQUENCE LISTING

```
<160> NUMBER OF SEQ ID NOS: 16

<210> SEQ ID NO 1
<211> LENGTH: 1158
<212> TYPE: DNA
<213> ORGANISM: Artificial
<220> FEATURE:
<223> OTHER INFORMATION: Fusion between DHFR and puromycin N-acetyl
      transferase
<220> FEATURE:
<221> NAME/KEY: CDS
<222> LOCATION: (1)..(1155)
<223> OTHER INFORMATION:
<220> FEATURE:
<221> NAME/KEY: misc_feature
<222> LOCATION: (1)..(597)
<223> OTHER INFORMATION: Fragment derived from puromycin N-acetyl
      transferase
<220> FEATURE:
<221> NAME/KEY: misc_feature
<222> LOCATION: (598)..(1155)
<223> OTHER INFORMATION: Fragment derived from DHFR

<400> SEQUENCE: 1 atg acc gag tac aag ccc acg gtg cgc ctc gcc acc cgc gac gac gtc    48
```

```
Met Thr Glu Tyr Lys Pro Thr Val Arg Leu Ala Thr Arg Asp Asp Val
1               5                   10                  15 ccc cgg gcc gta cgc acc ctc gcc gcc gcg ttc gcc gac tac ccc gcc         96
Pro Arg Ala Val Arg Thr Leu Ala Ala Ala Phe Ala Asp Tyr Pro Ala
                20                  25                  30 acg cgc cac acc gtc gac ccg gac cgc cac atc gag cgg gtc acc gag        144
Thr Arg His Thr Val Asp Pro Asp Arg His Ile Glu Arg Val Thr Glu
            35                  40                  45 ctg caa gaa ctc ttc ctc acg cgc gtc ggg ctc gac atc ggc aag gtg        192
Leu Gln Glu Leu Phe Leu Thr Arg Val Gly Leu Asp Ile Gly Lys Val
        50                  55                  60 tgg gtc gcg gac gac ggc gcc gcg gtg gcg gtc tgg acc acg ccg gag        240
Trp Val Ala Asp Asp Gly Ala Ala Val Ala Val Trp Thr Thr Pro Glu
65                  70                  75                  80 agc gtc gaa gcg ggg gcg gtg ttc gcc gag atc ggc ccg cgc atg gcc        288
Ser Val Glu Ala Gly Ala Val Phe Ala Glu Ile Gly Pro Arg Met Ala
                85                  90                  95 gag ttg agc ggt tcc cgg ctg gcc gcg cag caa cag atg gaa ggc ctc        336
Glu Leu Ser Gly Ser Arg Leu Ala Ala Gln Gln Gln Met Glu Gly Leu
            100                 105                 110 ctg gcg ccg cac cgg ccc aag gag ccc gcg tgg ttc ctg gcc acc gtc        384
Leu Ala Pro His Arg Pro Lys Glu Pro Ala Trp Phe Leu Ala Thr Val
        115                 120                 125 ggc gtc tcg ccc gac cac cag ggc aag ggt ctg ggc agc gcc gtc gtg        432
Gly Val Ser Pro Asp His Gln Gly Lys Gly Leu Gly Ser Ala Val Val
    130                 135                 140 ctc ccc gga gtg gag gcg gcc gag cgc gcc ggg gtg ccc gcc ttc ctg        480
Leu Pro Gly Val Glu Ala Ala Glu Arg Ala Gly Val Pro Ala Phe Leu
145                 150                 155                 160 gag acc tcc gcg ccc cgc aac ctc ccc ttc tac gag cgg ctc ggc ttc        528
Glu Thr Ser Ala Pro Arg Asn Leu Pro Phe Tyr Glu Arg Leu Gly Phe
                165                 170                 175 acc gtc acc gcc gac gtc gag gtg ccc gaa gga ccg cgc acc tgg tgc        576
Thr Val Thr Ala Asp Val Glu Val Pro Glu Gly Pro Arg Thr Trp Cys
            180                 185                 190 atg acc cgc aag ccc ggt gcc gtt cga cca ttg aac tgc atc gtc gcc        624
Met Thr Arg Lys Pro Gly Ala Val Arg Pro Leu Asn Cys Ile Val Ala
        195                 200                 205 gtg tcc caa aat atg ggg att ggc aag aac gga gac cta ccc tgg cct        672
Val Ser Gln Asn Met Gly Ile Gly Lys Asn Gly Asp Leu Pro Trp Pro
    210                 215                 220 ccg ctc agg aac gag ttc aag tac ttc caa aga atg acc aca acc tct        720
Pro Leu Arg Asn Glu Phe Lys Tyr Phe Gln Arg Met Thr Thr Thr Ser
225                 230                 235                 240 tca gtg gaa ggt aaa cag aat ctg gtg att atg ggt agg aaa acc tgg        768
Ser Val Glu Gly Lys Gln Asn Leu Val Ile Met Gly Arg Lys Thr Trp
                245                 250                 255 ttc tcc att cct gag aag aat cga cct tta aag gac aga att aat ata        816
Phe Ser Ile Pro Glu Lys Asn Arg Pro Leu Lys Asp Arg Ile Asn Ile
            260                 265                 270 gtt ctc agt aga gaa ctc aaa gaa cca cca cga gga gct cat ttt ctt        864
Val Leu Ser Arg Glu Leu Lys Glu Pro Pro Arg Gly Ala His Phe Leu
        275                 280                 285 gcc aaa agt ttg gat gat gcc tta aga ctt att gaa caa ccg gaa ttg        912
Ala Lys Ser Leu Asp Asp Ala Leu Arg Leu Ile Glu Gln Pro Glu Leu
    290                 295                 300 gca agt aaa gta gac atg gtt tgg ata gtc gga ggc agt tct gtt tac        960
Ala Ser Lys Val Asp Met Val Trp Ile Val Gly Gly Ser Ser Val Tyr
305                 310                 315                 320
```

```
cag gaa gcc atg aat caa cca ggc cac ctc aga ctc ttt gtg aca agg     1008
Gln Glu Ala Met Asn Gln Pro Gly His Leu Arg Leu Phe Val Thr Arg
                325                 330                 335 atc atg cag gaa ttt gaa agt gac acg ttt ttc cca gaa att gat ttg     1056
Ile Met Gln Glu Phe Glu Ser Asp Thr Phe Phe Pro Glu Ile Asp Leu
                340                 345                 350 ggg aaa tat aaa ctt ctc cca gaa tac cca ggc gtc ctc tct gag gtc     1104
Gly Lys Tyr Lys Leu Leu Pro Glu Tyr Pro Gly Val Leu Ser Glu Val
                355                 360                 365 cag gag gaa aaa ggc atc aag tat aag ttt gaa gtc tac gag aag aaa     1152
Gln Glu Glu Lys Gly Ile Lys Tyr Lys Phe Glu Val Tyr Glu Lys Lys
                370                 375                 380 gac taa                                                             1158
Asp
385

<210> SEQ ID NO 2
<211> LENGTH: 385
<212> TYPE: PRT
<213> ORGANISM: Artificial
<220> FEATURE:
<223> OTHER INFORMATION: Fusion between DHFR and puromycin N-acetyl
      transferase

<400> SEQUENCE: 2

Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
                20                  25                  30

Thr Arg His Thr Val Asp Pro Asp Arg His Ile Glu Arg Val Thr Glu
            35                  40                  45

Leu Gln Glu Leu Phe Leu Thr Arg Val Gly Leu Asp Ile Gly Lys Val
        50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu
                100                 105                 110

Leu Ala Pro His Arg Pro Lys Glu Pro Ala Trp Phe Leu Ala Thr Val
            115                 120                 125

Gly Val Ser Pro Asp His Gln Gly Lys Gly Leu Gly Ser Ala Val Val
        130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Val Pro Glu Gly Pro Arg Thr Trp Cys
                180                 185                 190

Met Thr Arg Lys Pro Gly Ala Val Arg Pro Leu Asn Cys Ile Val Ala
            195                 200                 205

Val Ser Gln Asn Met Gly Ile Gly Lys Asn Gly Asp Leu Pro Trp Pro
        210                 215                 220

Pro Leu Arg Asn Glu Phe Lys Tyr Phe Gln Arg Met Thr Thr Thr Ser
225                 230                 235                 240

Ser Val Glu Gly Lys Gln Asn Leu Val Ile Met Gly Arg Lys Thr Trp
                245                 250                 255
```

```
Phe Ser Ile Pro Glu Lys Asn Arg Pro Leu Lys Asp Arg Ile Asn Ile
            260                 265                 270

Val Leu Ser Arg Glu Leu Lys Glu Pro Pro Arg Gly Ala His Phe Leu
        275                 280                 285

Ala Lys Ser Leu Asp Asp Ala Leu Arg Leu Ile Glu Gln Pro Glu Leu
    290                 295                 300

Ala Ser Lys Val Asp Met Val Trp Ile Val Gly Gly Ser Ser Val Tyr
305                 310                 315                 320

Gln Glu Ala Met Asn Gln Pro Gly His Leu Arg Leu Phe Val Thr Arg
                325                 330                 335

Ile Met Gln Glu Phe Glu Ser Asp Thr Phe Phe Pro Gly Ile Asp Leu
            340                 345                 350

Gly Lys Tyr Lys Leu Leu Pro Glu Tyr Pro Gly Val Leu Ser Glu Val
        355                 360                 365

Gln Glu Glu Lys Gly Ile Lys Tyr Lys Phe Glu Val Tyr Glu Lys Lys
    370                 375                 380

Asp
385

<210> SEQ ID NO 3
<211> LENGTH: 906
<212> TYPE: DNA
<213> ORGANISM: Streptomyces alboniger
<220> FEATURE:
<221> NAME/KEY: gene
<222> LOCATION: (1)..(853)
<223> OTHER INFORMATION:
<220> FEATURE:
<221> NAME/KEY: CDS
<222> LOCATION: (254)..(853)
<223> OTHER INFORMATION:

<400> SEQUENCE: 3
gtcgacatcg cggccgaacc ggtcgtgagc ccctgggaca tcgccgccct ccagatcctc      60
gtggaggagg cgggcggcgt ctgcaccgac ctgctcggcg gctcgcccca gcgcgggacg     120
ggtgccctgt ccgccaaccc ggagctgcac cggctcgccg tggaggccct cgccgccccc     180
gcggccgcca cgaccggtgc cgccaccatc ccctgaccca cgccctgac ccctcacaag     240 gagacgacct tcc atg acc gag tac aag ccc acg gtg cgc ctc gcc acc        289
            Met Thr Glu Tyr Lys Pro Thr Val Arg Leu Ala Thr
             1               5                  10 cgc gac gac gtc ccc cgg gcc gta cgc acc ctc gcc gcc gcg ttc gcc       337
Arg Asp Asp Val Pro Arg Ala Val Arg Thr Leu Ala Ala Ala Phe Ala
        15                  20                  25 gac tac ccc gcc acg cgc cac acc gtc gac ccg gac cgc cac atc gag       385
Asp Tyr Pro Ala Thr Arg His Thr Val Asp Pro Asp Arg His Ile Glu
    30                  35                  40 cgg gtc acc gag ctg caa gaa ctc ttc ctc acg cgc gtc ggg ctc gac       433
Arg Val Thr Glu Leu Gln Glu Leu Phe Leu Thr Arg Val Gly Leu Asp
45                  50                  55                  60 atc ggc aag gtg tgg gtc gcg gac gac ggc gcc gcg gtg gcg gtc tgg       481
Ile Gly Lys Val Trp Val Ala Asp Asp Gly Ala Ala Val Ala Val Trp
                65                  70                  75 acc acg ccg gag agc gtc gaa gcg ggg gcg gtg ttc gcc gag atc ggc       529
Thr Thr Pro Glu Ser Val Glu Ala Gly Ala Val Phe Ala Glu Ile Gly
    80                  85                  90 ccg cgc atg gcc gag ttg agc ggt tcc cgg ctg gcc gcg cag caa cag       577
Pro Arg Met Ala Glu Leu Ser Gly Ser Arg Leu Ala Ala Gln Gln Gln
            95                  100                 105
```

| | | |
|---|---|---|
| atg gaa ggc ctc ctg gcg ccg cac cgg ccc aag gag ccc gcg tgg ttc<br>Met Glu Gly Leu Leu Ala Pro His Arg Pro Lys Glu Pro Ala Trp Phe<br>110                       115                     120 | | 625 |
| ctg gcc acc gtc ggc gtc tcg ccc gac cac cag ggc aag ggt ctg ggc<br>Leu Ala Thr Val Gly Val Ser Pro Asp His Gln Gly Lys Gly Leu Gly<br>125                       130                     135                    140 | | 673 |
| agc gcc gtc gtg ctc ccc gga gtg gag gcg gcc gag cgc gcc ggg gtg<br>Ser Ala Val Val Leu Pro Gly Val Glu Ala Ala Glu Arg Ala Gly Val<br>145                       150                     155 | | 721 |
| ccc gcc ttc ctg gag acc tcc gcg ccc cgc aac ctc ccc ttc tac gag<br>Pro Ala Phe Leu Glu Thr Ser Ala Pro Arg Asn Leu Pro Phe Tyr Glu<br>                   160                     165                    170 | | 769 |
| cgg ctc ggc ttc acc gtc acc gcc gac gtc gag gtg ccc gaa gga ccg<br>Arg Leu Gly Phe Thr Val Thr Ala Asp Val Glu Val Pro Glu Gly Pro<br>175                       180                     185 | | 817 |
| cgc acc tgg tgc atg acc cgc aag ccc ggt gcc tga cgcccgcccc<br>Arg Thr Trp Cys Met Thr Arg Lys Pro Gly Ala<br>190                     195 | | 863 |
| acgacccgca gcgcccgacc gaaaggagcg cacgacccca tgg | | 906 |

<210> SEQ ID NO 4
<211> LENGTH: 199
<212> TYPE: PRT
<213> ORGANISM: Streptomyces alboniger

<400> SEQUENCE: 4

Met Thr Glu Tyr Lys Pro Thr Val Arg Leu Ala Thr Arg Asp Asp Val
1               5                  10               15

Pro Arg Ala Val Arg Thr Leu Ala Ala Phe Ala Asp Tyr Pro Ala
               20                  25               30

Thr Arg His Thr Val Asp Pro Asp Arg His Ile Glu Arg Val Thr Glu
             35                  40               45

Leu Gln Glu Leu Phe Leu Thr Arg Val Gly Leu Asp Ile Gly Lys Val
    50                  55                  60

Trp Val Ala Asp Asp Gly Ala Ala Val Ala Val Trp Thr Thr Pro Glu
65               70                  75              80

Ser Val Glu Ala Gly Ala Val Phe Ala Glu Ile Gly Pro Arg Met Ala
               85                  90               95

Glu Leu Ser Gly Ser Arg Leu Ala Ala Gln Gln Gln Met Glu Gly Leu
             100                 105              110

Leu Ala Pro His Arg Pro Lys Glu Pro Ala Trp Phe Leu Ala Thr Val
            115                 120              125

Gly Val Ser Pro Asp His Gln Gly Lys Gly Leu Gly Ser Ala Val Val
    130                135                140

Leu Pro Gly Val Glu Ala Ala Glu Arg Ala Gly Val Pro Ala Phe Leu
145               150                  155              160

Glu Thr Ser Ala Pro Arg Asn Leu Pro Phe Tyr Glu Arg Leu Gly Phe
               165                  170              175

Thr Val Thr Ala Asp Val Glu Val Pro Glu Gly Pro Arg Thr Trp Cys
            180                 185              190

Met Thr Arg Lys Pro Gly Ala
            195

<210> SEQ ID NO 5
<211> LENGTH: 5307
<212> TYPE: DNA
<213> ORGANISM: Mus musculus
<220> FEATURE:

<210> NAME/KEY: mRNA
<222> LOCATION: (1)..(5307)
<223> OTHER INFORMATION:
<220> FEATURE:
<221> NAME/KEY: CDS
<222> LOCATION: (477)..(1040)
<223> OTHER INFORMATION:

<400> SEQUENCE: 5

```
aggacgcgct ggatcttagg cttcccgcag acctgaagaa ccggcttaga accgtttgcc      60
tccccgggcc tgggccggcg gcagtagagc ctcccgacgc ggatttcccg cggggcattg     120
cagtgtgcag aagagccggc ctgctaggag cgcgagcgcg cggccgcact ttctcgcgcc     180
tgcgcgcgcg cacgcctcaa cctgtgcggg accggccttg gggcggagc cttagctaca      240 caaatagaat gcgcggcggg ccttggtggg ggcggggcct tagctgcaca aataggatgc     300
gcggcgggcc ttggtagggg cggagcctta gctgcacaaa taggatgcgc ggcgggcctt     360 ggtggggcg gggcctaagc tgcgcaagtg gtacacagct cagggctgcg atttcgcgcc      420
aaacttgacg gcaatcctag cgtgaaggct ggtaggattt tatccccgct gccatc atg     479
                                                                 Met
                                                                  1
```

| | | | | | | | | | | | | | | | | |
|---|---|---|---|---|---|---|---|---|---|---|---|---|---|---|---|---|
| gtt | cga | cca | ttg | aac | tgc | atc | gtc | gcc | gtg | tcc | caa | aat | atg | ggg | att | 527 |
| Val | Arg | Pro | Leu | Asn | Cys | Ile | Val | Ala | Val | Ser | Gln | Asn | Met | Gly | Ile | |
| | | | 5 | | | | | 10 | | | | | 15 | | | |

| ggc | aag | aac | gga | gac | cta | ccc | tgg | cct | ccg | ctc | agg | aac | gag | ttc | aag | 575 |
|---|---|---|---|---|---|---|---|---|---|---|---|---|---|---|---|---|
| Gly | Lys | Asn | Gly | Asp | Leu | Pro | Trp | Pro | Pro | Leu | Arg | Asn | Glu | Phe | Lys | |
| | | | 20 | | | | | 25 | | | | | 30 | | | |

| tac | ttc | caa | aga | atg | acc | aca | acc | tct | tca | gtg | gaa | ggt | aaa | cag | aat | 623 |
|---|---|---|---|---|---|---|---|---|---|---|---|---|---|---|---|---|
| Tyr | Phe | Gln | Arg | Met | Thr | Thr | Thr | Ser | Ser | Val | Glu | Gly | Lys | Gln | Asn | |
| | 35 | | | | | 40 | | | | | 45 | | | | | |

| ctg | gtg | att | atg | ggt | agg | aaa | acc | tgg | ttc | tcc | att | cct | gag | aag | aat | 671 |
|---|---|---|---|---|---|---|---|---|---|---|---|---|---|---|---|---|
| Leu | Val | Ile | Met | Gly | Arg | Lys | Thr | Trp | Phe | Ser | Ile | Pro | Glu | Lys | Asn | |
| 50 | | | | | 55 | | | | | 60 | | | | | 65 | |

| cga | cct | tta | aag | gac | aga | att | aat | ata | gtt | ctc | agt | aga | gaa | ctc | aaa | 719 |
|---|---|---|---|---|---|---|---|---|---|---|---|---|---|---|---|---|
| Arg | Pro | Leu | Lys | Asp | Arg | Ile | Asn | Ile | Val | Leu | Ser | Arg | Glu | Leu | Lys | |
| | | | 70 | | | | | 75 | | | | | 80 | | | |

| gaa | cca | cca | cga | gga | gct | cat | ttt | ctt | gcc | aaa | agt | ttg | gat | gat | gcc | 767 |
|---|---|---|---|---|---|---|---|---|---|---|---|---|---|---|---|---|
| Glu | Pro | Pro | Arg | Gly | Ala | His | Phe | Leu | Ala | Lys | Ser | Leu | Asp | Asp | Ala | |
| | | 85 | | | | | 90 | | | | | 95 | | | | |

| tta | aga | ctt | att | gaa | caa | ccg | gaa | ttg | gca | agt | aaa | gta | gac | atg | gtt | 815 |
|---|---|---|---|---|---|---|---|---|---|---|---|---|---|---|---|---|
| Leu | Arg | Leu | Ile | Glu | Gln | Pro | Glu | Leu | Ala | Ser | Lys | Val | Asp | Met | Val | |
| | | | 100 | | | | | 105 | | | | | 110 | | | |

| tgg | ata | gtc | gga | ggc | agt | tct | gtt | tac | cag | gaa | gcc | atg | aat | caa | cca | 863 |
|---|---|---|---|---|---|---|---|---|---|---|---|---|---|---|---|---|
| Trp | Ile | Val | Gly | Gly | Ser | Ser | Val | Tyr | Gln | Glu | Ala | Met | Asn | Gln | Pro | |
| | 115 | | | | | 120 | | | | | 125 | | | | | |

| ggc | cac | ctc | aga | ctc | ttt | gtg | aca | agg | atc | atg | cag | gaa | ttt | gaa | agt | 911 |
|---|---|---|---|---|---|---|---|---|---|---|---|---|---|---|---|---|
| Gly | His | Leu | Arg | Leu | Phe | Val | Thr | Arg | Ile | Met | Gln | Glu | Phe | Glu | Ser | |
| 130 | | | | | 135 | | | | | 140 | | | | | 145 | |

| gac | acg | ttt | ttc | cca | gaa | att | gat | ttg | ggg | aaa | tat | aaa | ctt | ctc | cca | 959 |
|---|---|---|---|---|---|---|---|---|---|---|---|---|---|---|---|---|
| Asp | Thr | Phe | Phe | Pro | Glu | Ile | Asp | Leu | Gly | Lys | Tyr | Lys | Leu | Leu | Pro | |
| | | | 150 | | | | | 155 | | | | | 160 | | | |

| gaa | tac | cca | ggc | gtc | ctc | tct | gag | gtc | cag | gag | gaa | aaa | ggc | atc | aag | 1007 |
|---|---|---|---|---|---|---|---|---|---|---|---|---|---|---|---|---|
| Glu | Tyr | Pro | Gly | Val | Leu | Ser | Glu | Val | Gln | Glu | Glu | Lys | Gly | Ile | Lys | |
| | | 165 | | | | | 170 | | | | | 175 | | | | |

| tat | aag | ttt | gaa | gtc | tac | gag | aag | aaa | gac | taa | cagg | aagatg | ctttcaagtt | | | 1060 |
|---|---|---|---|---|---|---|---|---|---|---|---|---|---|---|---|---|
| Tyr | Lys | Phe | Glu | Val | Tyr | Glu | Lys | Lys | Asp | | | | | | | |
| | 180 | | | | | 185 | | | | | | | | | | |

```
ctctgctccc ctcctaaagc tatgcatttt tataagacca tgggactttt gctggcttta    1120
gatctatgag taattatttc tttagggagg ggtagttgga agaattgttt gttttgtgat    1180
```

```
cctgggatg gaacctaaga cccagtgcgt gctgagcaaa tgctatactg ctgagccacc   1240
ccaaccctag cccctatata attctaaaca atatgttgtc atttcccagt aatctaacaa   1300
ggttatagta aaagtgcctt aagaaatgtc acttgctata aaggtctcag tgcccctccc   1360
atgagacctc aagtggctcc ccagcatatg cacagggtac tgtgtgtaca agagacccca   1420
gtgatgtaga gccctggag catgagcaga tgtgtgggct cataaaagta ggagctaggc   1480
aggtaagtcc aaagggcaga aacaggtttt aaacagcaga gctggaactc agactataaa   1540
gaaaattcca tcaaagtaga gactggatta ttgtatgcac atcacacttg cagcaaagct   1600
ctgctcactc agacagaaaa tcagtaaatg gagaactcca ttgtgttcca tggagacgag   1660
agcaggtgga agattatgta agatctgaaa cactgaaatt gtctgcttct catcttcagt   1720
gagattccaa aggatagtac agtgacagaa caagaatagg cactctctac aaaaaaaaga   1780
aagaaaaaac taagtaatag caagcataat agctactgtt aagaactcag agataatgaa   1840
ttgagaatgg atactgcttg aaatgaaaat ttaataagtt agaaactaaa ctttataaaa   1900
ataaaaaaat gagcattaaa atggctttcc tcatctcagc agggtttcag atcatcaggt   1960
cagagaaagt atttctgcct ggccttgtaa attagtatgg tcttttttta tcttttactt   2020
gacaatttcc tacatgttta cgatgtgtct taatcatacc aggtcctcat ccccactccc   2080
ccactacctt tgtatcttct ttctcttttc ataaccttct gaaaccagtc attgctttct   2140
tcatgttcct gcatgtgtgc tgtccactgg agtacgggca gcctgccagt ggacacacac   2200
acacacacac acacacacac acacacacac acacacagag ccatcagtta ccaatagctc   2260
ttcagctggg tgcagtctta ggagcctctc ctccatccaa gctagaatat gggtctgcag   2320
atcaccacag ctgctgtgag cttgtgagtg tggtgtccat gccatgtcca gaaggcagca   2380
ttatatatac atggccctat tccccaggct tcaggccttc attctttcca ccacttcttc   2440
agtgctccct gagccttaga caagtctact gatagaaatg gtctgttcag agctgaatag   2500
taaacagtca cttagtctct cactttgat cagccttgtg tctgtaagct ggatgctctc   2560
tactgaaaaa aaaaaaaaaa aaaacagaac ttcttctcca accagggtta agagcactaa   2620
tacagggtat aaacacaggt atttagaaag cactctgaaa acctagccat ttaacaaagc   2680
agcagtagta ggtttgtcct tagaacccat gacttccaca ccacaggcat ttgaccagtt   2740
ttgcagtact agacatgaat tgtctcctat agagccggcc tcaaatccaa ctaggaagca   2800
ttgacaggca tgccattgtt gttcagtaga aactgtaaca tgcagggcct accaccaact   2860
aagtccataa aagcttttct ccctggtgat gtgctcggca ccttctggcg ctgaaaactg   2920
tccagtgaag gaggaagttt ccaggcagct ccagattgat tctctatgtc ctgcaagtaa   2980
atgtgttgta aatgtgcctt caacagtagg ggcttgtcat ctggctacga caggcaacca   3040
agagcgatgg caaaagatgt gttgttttgg gagcctcctt aactagttac ttttaagggt   3100
gccccacacc tggcactgag agtttcattt aataacctag gtcttcattt agtaagcatt   3160
gtccaccagt gtgtaggatg cctccattca aacttttttc tttagttata attacctgat   3220
aaccatgaac aaagagatga actcaaagag gcagagagtc tgctgagcta gcccatgaag   3280
caggtgagcc agtttgtgtt atgtagcagt ttcctctaag gtcaaaacct gtcttagaag   3340
gaagctgttt tgacataaga cggtatagag gagctagaag aagagaatat tctaagggaa   3400
gctgggaact tccttaagct cagcaaatac acaactttaga agatcttaaa attgaccagg   3460
tacactagac tcctcccctcc ccaagcatag ataagcaatg attgccgagg ggctctgaga   3520
```

```
cacgctgagc tgtctagaag accaactgag cctcctggca aagcagagac cagcagagct    3580
gtctgaagga ggcttggacc taccgaactc cctagaaaga gcactggaac ctgttgagct    3640
gcctgtaggt tgtctaatac actccaggtt tcctgagctg tgactctgct ggaacgggct    3700
tttggtgatg caattttgat ggtctccttc ctttgaacgt ccatatctgg ggttaacaga    3760
catttgctcc tgtctctcca ggaggtgtgt tatacaatga tttggatccc tggtgctcag    3820
gcagaggcaa gtacagtagc atatgtttgt aaccctggca gtggtgtggt atgggagaga    3880
ctggcagtgt atttgcaagc cagactgacc caagaaagaa agaaaaaatt taattgtttc    3940
agcatctttt aaatttggaa aaaagcataa atgtcaaaga ataattact atgtctataa    4000 aatacaatat ttgcagcact tgaaaaggat gtggccctaa caggaaagtt cttcaggaaa    4060
agaaacacac acacaaaatc tagtattagt atgtctaaga gtaatatata ttaaaaatag    4120
ttgacaatat cagacttagt gttatttct gtttgtcttc tatgattagg attttttgga     4180
aacttttata gagaaattat ttaaactatt aagtcacagc ctttgttttc aacaggaaaa    4240
tgagggtata gagcattgag aggaaaaatg attttccaaa agtcatccat caagagagag    4300
agaccagacc atacaaaaga aaaagtcaa ttctatagaa cagttgcaca tcaaataaag     4360
caatagcgct ttcttgcaat gaacataacc tgaaagccac caatatccag aatttgtagg    4420
actcagtgac tcagtcagaa aaagaaacaa gttatttaca gaggaaattg aagtggccaa    4480
tgcagagctg aaccttctac cagaaggag agaggcaggg gaggaaatta catgtgccag     4540
tctcaccatc tttagactaa aatgttgaca tctcccagag ctagggatgc tatgctcagc    4600
acgcagcagt tcactgtgg ataagaccaa gagaacacct catacatgcc aaaacgaaag     4660
acaaaagcac cctggaaatc tagacacaag gaaattgtcg tctggctatt ttagtatgag    4720
ttctctccaa tgtgtattct gaaacaattc agtgaagtg gtgtgtgtgg taggatgcac     4780
cagaaagcac agttgggata tgggaaaaca agaaacctag ttcaaggtca ttaagcagat    4840
tcccattgac aacccgggaa actgagggag gaagaaagct ggagtgtgta gatcctgatc    4900
gttgtttgca cgatgttcca cactgccagc ttgttgctct gtgtaaaccg gacacactcc    4960
aactgccaag gtcccaagct gctaacataa atgcaaagaa tacgaaacac tagcaattcc    5020
atgtttctgc tactttctac ataaaaaaaa gtgcacagcc cagtaattta tttgaaatat    5080
aatatccatc agggtgaggg taagggtgat aatcatagct tccaccaaag cattgtgtat    5140
actgaaaagg agacatgata cgttttgtg ttagaaggcg aggtttcagg tgggctttga     5200
atttggtttg actgagactc attgagtttg aggtgtcttt aggaaaggaa gaaagaaggg    5260
aacaaaaaat aaaagcaat ggaacatgc aaaaaaaaaa aaaaaa                     5307
```

<210> SEQ ID NO 6
<211> LENGTH: 187
<212> TYPE: PRT
<213> ORGANISM: Mus musculus

<400> SEQUENCE: 6

```
Met Val Arg Pro Leu Asn Cys Ile Val Ala Val Ser Gln Asn Met Gly
  1               5                  10                  15

Ile Gly Lys Asn Gly Asp Leu Pro Trp Pro Leu Arg Asn Glu Phe
             20                  25                  30

Lys Tyr Phe Gln Arg Met Thr Thr Thr Ser Ser Val Glu Gly Lys Gln
         35                  40                  45

Asn Leu Val Ile Met Gly Arg Lys Thr Trp Phe Ser Ile Pro Glu Lys
     50                  55                  60
```

-continued

Asn Arg Pro Leu Lys Asp Arg Ile Asn Ile Val Leu Ser Arg Glu Leu
 65                  70                  75                  80

Lys Glu Pro Pro Arg Gly Ala His Phe Leu Ala Lys Ser Leu Asp Asp
                 85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Lys Gly Ile
                165                 170                 175

Lys Tyr Lys Phe Glu Val Tyr Glu Lys Lys Asp
            180                 185

<210> SEQ ID NO 7
<211> LENGTH: 21
<212> TYPE: DNA
<213> ORGANISM: Artificial
<220> FEATURE:
<223> OTHER INFORMATION: PCR primer

<400> SEQUENCE: 7
ccacctcgga atcttcaatg c                                       21

<210> SEQ ID NO 8
<211> LENGTH: 43
<212> TYPE: DNA
<213> ORGANISM: Artificial
<220> FEATURE:
<223> OTHER INFORMATION: PCR primer

<400> SEQUENCE: 8
gatgcagttc aatggtcgaa cggcaccggg cttgcgggtc atg                43

<210> SEQ ID NO 9
<211> LENGTH: 43
<212> TYPE: DNA
<213> ORGANISM: Artificial
<220> FEATURE:
<223> OTHER INFORMATION: PCR primer

<400> SEQUENCE: 9
catgacccgc aagcccggtg ccgttcgacc attgaactgc atc                43

<210> SEQ ID NO 10
<211> LENGTH: 21
<212> TYPE: DNA
<213> ORGANISM: Artificial
<220> FEATURE:
<223> OTHER INFORMATION: PCR primer

<400> SEQUENCE: 10
cggaaggagc tgactgggtt g                                       21

<210> SEQ ID NO 11
<211> LENGTH: 21
<212> TYPE: DNA
<213> ORGANISM: Artificial
<220> FEATURE:

```
<223> OTHER INFORMATION: Probe

<400> SEQUENCE: 11
tcaccgagct gcaagaactc t                                      21

<210> SEQ ID NO 12
<211> LENGTH: 17
<212> TYPE: DNA
<213> ORGANISM: Artificial
<220> FEATURE:
<223> OTHER INFORMATION: Probe

<400> SEQUENCE: 12
tccgcgaccc acacctt                                           17

<210> SEQ ID NO 13
<211> LENGTH: 17
<212> TYPE: DNA
<213> ORGANISM: Artificial
<220> FEATURE:
<223> OTHER INFORMATION: Nucleotidic part of TaqMan probe

<400> SEQUENCE: 13
acgcgcgtcg ggctcga                                           17

<210> SEQ ID NO 14
<211> LENGTH: 20
<212> TYPE: DNA
<213> ORGANISM: Artificial
<220> FEATURE:
<223> OTHER INFORMATION: probe

<400> SEQUENCE: 14
acaccgagga ccaggttgtc                                        20

<210> SEQ ID NO 15
<211> LENGTH: 19
<212> TYPE: DNA
<213> ORGANISM: Artificial
<220> FEATURE:
<223> OTHER INFORMATION: probe

<400> SEQUENCE: 15
cccagcatca aaggtggaa                                         19

<210> SEQ ID NO 16
<211> LENGTH: 27
<212> TYPE: DNA
<213> ORGANISM: Artificial
<220> FEATURE:
<223> OTHER INFORMATION: Nucleotific part of TaqMan probe

<400> SEQUENCE: 16
cctgcgactt caacagtgac tcccact                                27
```